(12) United States Patent
Hongo et al.

(10) Patent No.: US 7,745,499 B2
(45) Date of Patent: Jun. 29, 2010

(54) METAL COLLOID SOLUTION

(75) Inventors: Tomoko Hongo, Nobeoka (JP); Naoko Hamasaki, Nobeoka (JP); Shoichi Ide, Nobeoka (JP); Fumihiko Yamaguchi, Nobeoka (JP); Mitsunori Kubozaki, Miyazaki (JP)

(73) Assignee: Asahi Kasei Medical Co., Ltd, Tokyo (JP)

( * ) Notice: Subject to any disclaimer, the term of this patent is extended or adjusted under 35 U.S.C. 154(b) by 717 days.

(21) Appl. No.: 10/564,837

(22) PCT Filed: Jul. 16, 2004

(86) PCT No.: PCT/JP2004/010193

§ 371 (c)(1),
(2), (4) Date: Apr. 17, 2006

(87) PCT Pub. No.: WO2005/007328

PCT Pub. Date: Jan. 27, 2005

(65) Prior Publication Data

US 2006/0235085 A1    Oct. 19, 2006

(30) Foreign Application Priority Data

Jul. 17, 2003  (JP) .................. 2003-275847
Dec. 19, 2003  (JP) .................. 2003-422496

(51) Int. Cl.
*C09K 3/00* (2006.01)
(52) U.S. Cl. .................. 516/97; 516/77; 516/198
(58) Field of Classification Search .................. 516/97
See application file for complete search history.

(56) References Cited

U.S. PATENT DOCUMENTS 6,797,169 B1    9/2004    Ide et al.

FOREIGN PATENT DOCUMENTS

| | | |
|---|---|---|
| CN | 1179723 | 4/1998 |
| DE | 19803891 A1 * | 5/1999 |
| DE | 198 03 891 | 8/1999 |
| DE | 198 52 547 | 5/2000 |
| EP | 0 845 265 | 6/1998 |
| JP | 62-279834 | 12/1987 |
| JP | 63-63726 | 3/1988 |
| JP | 7-132215 | 5/1995 |
| JP | 8-141388 | 6/1996 |
| JP | 8-240823 | 9/1996 |
| JP | 2002-060805 * | 2/2002 |
| JP | 2002-60805 | 2/2002 |
| JP | 2002-102679 | 4/2002 |
| JP | 2002-180110 * | 6/2002 |
| JP | 2003-193119 | 7/2003 |
| WO | WO 97/06813 | 2/1997 |
| WO | 02/087749 | 11/2002 |

OTHER PUBLICATIONS

Meltzer et al. "Filtration in the Pharmaceutical Industry", Marcel Dekker, New York, 1998, p. 548-559 and 636-637.*
Tateishi et al. "Scrapie Removal using Planova Removal Filters", Biological (2001) 29, p. 17-25.*
Causserand et al., "Study of the effects of defects in ultrafiltration membranes on the water flux and the molecular weight cut-off", Desalination, Sep. 10, 2002,149, Issue 1-3, pp. 485-491.*
Catalogue of Planova Filters, Virus Removal for Biotherapeutic Products, Asahi Kasei Corporation, 2001, pp. 2-7.
Printout of homepages of Asahi Kasei Medical.
H. Murakami et al., "Novel Validation Method of Virus-Removability for biological Cell Culture Products Using Polymeric Membrane Filters", Animal Cell Technology: Basic & Applied Aspects, vol. 4, 1992, pp. 87-102.
European Search Report—Feb. 9, 2009—EP 04 74 7659.

* cited by examiner

*Primary Examiner*—Ling-Siu Choi
*Assistant Examiner*—Chun-Cheng Wang
(74) *Attorney, Agent, or Firm*—Young & Thompson

(57) ABSTRACT

A colloid solution that exhibits storage stability and pH stability, being useful as viral substitute particles for use in an integrity test for virus removal membrane. In particular, a metal colloid solution characterized in that it comprises metal particles or metal compound particles of 1 to 100 nm average diameter, a water soluble high-molecular-weight dispersant having an N group and water and/or a water soluble organic solvent, the metal colloid solution being stable for a prolonged period of time and being stable in at least pH values ranging from 4 to 11.

15 Claims, 2 Drawing Sheets

METAL COLLOID SOLUTION

FIELD OF THE INVENTION

The present invention relates to a metal colloid solution excelling in storage stability, temperature stability, and pH stability, useful as viral substitute particles for utilization in an integrity test for a virus removal membrane, for example, and to a method for producing the same.

BACKGROUND ART

Metal colloid particles with an average particle diameter of 1-100 nm are used in a number of functional materials because of small particle diameter and large surface area. When added to water, however, such particles easily aggregate due to a strong interparticle force. It is difficult to uniformly disperse the metal colloid particles. In addition, to stably disperse metal colloid particles, the pH of the solution must be controlled in a specific range. The applicable pH range is unduly limited (Patent Document 1).

A membrane integrity test method using substitute particles in a virus removal membrane has been disclosed. The integrity test is a test for confirming performance of virus removal membranes for removing viruses from solutions containing proteins, physiological active products, and the like after use (or occasionally before use). The integrity test methods include (1) a bubble pointing method, (2) a method of measuring the proportion of large pores in a pore diameter distribution of the membrane (for example, a method of using a low liquid-liquid interfacial tension), and (3) a method of filtering viral substitute particles. Of these methods, the method of filtering viral substitute particles is highly reliable since the principle of the method is particle sieving filtration which is the same as virus removal and, therefore, can obtain correlation of characteristics of the same type of mechanisms as virus removal. Particularly, there is an excellent correlation between removability of a gold colloid, used as viral substitute particles, by filtration and the virus removal capability of a membrane. In the integrity test, the membrane needs to be washed after use as a virus removal membrane to reduce the amount of residue in the membrane to the maximum extent possible. A solution such as an alkaline solution may be used as washing agent. Since a conventional gold colloid solution with only a limited pH range could be used, post-washing for strict control of the pH of the membrane after washing with washing agent was necessary. The operation was very complicated (Patent Document 2, Non-patent Document 1).

In the integrity test of a virus removal membrane for removing small viruses with a diameter of 20-25 nm such as parvovirus, even substitute for viral particles having correlation with virus removal capability has not existed. To exhibit characteristics of both consistent high removability of small viruses and high protein permeability, the membrane must have a special structure. The integrity test for the virus removal membrane having such a membrane structure must detect a very small difference in pore diameters. There have been no metal colloid solutions usable for such a purpose to date (Patent Document 3).

(Patent Document 1) JP-A-08-141388
(Patent Document 2) JP-A-07-132215
(Patent Document 3) WO 01/014047

(Non-patent document 1) Hiroki Murakami (Etd.), Animal Cell Technology; Basic & Applied Aspects, Netherland, Kluwer Academic Publishers, Vol. 4, 1992, p.87-102

DISCLOSURE OF THE INVENTION

Problems to be Solved by the Invention

An object of the present invention is to provide a novel colloid solution excelling in storage stability, temperature stability, and pH stability, useful in an integrity test for virus removal membrane, for example.

Means for Solving the Problems

As a result of extensive studies to achieve the above objects, the present inventors have found that a metal colloid solution containing metal particles or metal compound particles having an average particle diameter of 1-100 nm, a water-soluble high molecular weight dispersant containing an N group, and water and/or a water-soluble organic solvent, and having at least a pH in the range of 4-11 can achieve the above object. This finding has led to the completion of the present invention.

Specifically, the present invention includes:

[1] A colloid solution of metal particles or metal compound particles comprising at least (1) metal particles or metal compound particles having an average particle diameter of 1-100 nm, (2) a water-soluble high molecular weight dispersant containing an N group, and (3) water and/or a water-soluble organic solvent, and having the following properties (a) and (b):

(a) exhibiting a change in the maximum absorption wavelength in the range from −2.0 nm to +2.0 nm before and after being stored at room temperature for 180 days at a constant pH in the range from pH4 to pH11 and (b) exhibiting a change in the maximum absorption wavelength in the range from −2.0 nm to +2.0 nm when stored at 50° C. for one year at pH5.

[2] The colloid solution according to [1], further comprising (4) a surfactant and/or a chelating agent.

[3] The colloid solution according to [1] or [2], used with a porous cellulose membrane.

[4] The colloid solution according to any of [1] to [3], comprising (4) at least a surfactant or a surfactant and a chelating agent.

[5] The colloid solution according to [3] or [4], wherein the porous cellulose membrane is a virus removal membrane.

[6] The colloid solution according to any of [3] to [5], wherein the porous cellulose membrane comprises a regenerated cellulose.

[7] The colloid solution according to [1] or [2], which is a colloid solution of metal particles or metal compound particles further comprising (4) at least a chelating agent, but not a surfactant, and is used with a porous membrane of synthetic polymer.

[8] The colloid solution according to [7], wherein the porous membrane of synthetic polymer is a virus removal membrane.

[9] The colloid solution according to [7], wherein the porous membrane of synthetic polymer comprises a thermoplastic polymer of which the surface is hydrophilized.

[10] The colloid solution according to [9], wherein the thermoplastic polymer is either polyvinylidene fluoride or polyether sulfone.

[11] The colloid solution according to any of [1] to [10], achieving a colloid recovery rate of 70% or more when the colloid solution is filtered through a collection test porous membrane, and satisfying the following conditions:

(average pore diameter (nm) of the collection test porous membrane)−(average particle diameter (nm) of colloid)>10 nm.

[12] The colloid solution according to any of [1] to [11], used with a porous membrane, achieving a colloid recovery rate of 70% or more when the colloid solution is filtered through a collection test porous membrane made of the same material as the porous membrane, and satisfying the following conditions:

(average pore diameter (nm) of the collection test porous membrane)−(average particle diameter (nm) of colloid)>10 nm.

[13] The colloid solution according to [11] or [12], wherein the collection test porous membrane is a virus removal membrane.

[14] The colloid solution according to any of [1] to [13], wherein the particles in the colloid solution are metal particles alone.

[15] The colloid solution according to any of [1] to [14], wherein the colloid solution contains metal particles or metal compound particles which can be identified in the visible range.

[16] The colloid solution according to any of [1] to [15], wherein the shape of the metal particles or metal compound particles in the colloid solution is isotropic or approximately isotropic (the particles having a ratio of major axis/minor axis preferably from 1 to 2, and more preferably from 1 to 1.8).

[17] The colloid solution according to any of [1] to [16], wherein the metal particles comprise at least one of gold, silver, platinum, rhodium, palladium, ruthenium, iridium, osmium, iron, and copper.

[18] The colloid solution according to any of [1] to [16], wherein the metal particles are gold particles.

[19] The colloid solution according to any of [1] to [18], wherein the virus removal membrane has an average pore diameter of 10 to 100 nm.

[20] The colloid solution according to any of [1] to [19], wherein the percent of variation in the diameter distribution of the metal particles or the metal compound particles is 30% or less.

[21] The colloid solution according to any of [1] to [20], containing metal particles or metal compound particles having an average particle diameter of 15 to 40 nm and the percent of variation in the particle diameter distribution of 27% or less.

[22] The colloid solution according to any of [1] to [21], containing metal particles or metal compound particles having an average particle diameter of 15 to 25 nm and the percent of variation in the particle diameter distribution of 27% or less.

[23] The colloid solution according to any of [1] to [21], containing metal particles or metal compound particles having an average particle diameter of 25 to 40 nm (preferably from 27 to 37 nm) and the percent of variation in the particle diameter distribution of 27% or less.

[24] The colloid solution according to any of [1] to [23], wherein the N group is a pyrrolidone group.

[25] The colloid solution according to any of [1] to [24], wherein the water-soluble high molecular weight dispersant containing an N group is poly(vinylpyrrolidone) or a poly(vinylpyrrolidone) copolymer.

[26] The colloid solution according to any of [1] to [25], wherein the water-soluble high molecular weight dispersant containing an N group has a molecular weight of 1,000 to 2,000,000.

[27] The colloid solution according to any of [2] to [6] and [11] to [26], wherein the surfactant is a nonionic surfactant or an anionic surfactant.

[28] The colloid solution according to any of [2] to [6] and [11] to [27], wherein the surfactant is dodecylsulfuric acid or its salt (preferably sodium dodecylsulfate).

[29] The colloid solution according to any of [2] to [28], wherein the chelating agent is at least one of tripolyphosphoric acid, polyacrylic acid, polyacrylic acid copolymer, ethylenediaminetetraacetic acid, and salts thereof (preferably at least one of sodium tripolyphosphate, sodium polyacrylate, sodium polyacrylic acid copolymer, and sodium ethylenediaminetetraacetate).

[30] The colloid solution according to any of [2] to [29], wherein the surfactant or chelating agent is included in the colloid solution in an amount of 0.001 to 5 wt %.

[31] The colloid solution according to any of [2] to [30], wherein the polyacrylic acid, polyacrylic acid copolymer, or salts thereof have a molecular weight in the range of 100 to 10,000.

[32] The colloid solution according to any of [1] to [31], wherein the amount of the metal particles or the metal compound particles in the colloid solution is from 0.0001 to 0.1 wt %.

[33] The colloid solution according to any of [1] to [32], wherein the amount of the water-soluble high molecular weight dispersant containing an N group in the colloid solution is from 0.001 to 10 wt %.

[34] The colloid solution according to any of [1] to [33], wherein the amount of the metal particles or the metal compound particles in the colloid solution is from 0.001 to 0.08 wt %.

[35] The colloid solution according to any of [1] to [34], wherein the amount of the water-soluble high molecular weight dispersant containing an N group in the colloid solution is from 0.01 to 5 wt %.

[36] The colloid solution according to any of [1] to [35], exhibiting a change in the maximum absorption wavelength in the range from −1.5 nm to +1.5 nm (preferably from −1.0 nm to +1.0 nm) before or after being stored the colloid solution at room temperature for 180 days at a constant pH in the range from pH4 to pH11.

[37] The colloid solution according to any of [1] to [36], exhibiting a change in the maximum absorption wavelength in the range from −1.7 nm to +1.7 nm (preferably from −1.5 nm to +1.5 nm, and more preferably from −1.0 nm to +1.0 nm) before or after being stored the colloid solution at 50° C. for 1 year at pH5.

[38] The colloid solution according to [2], prepared by adding a water-soluble high molecular weight dispersant containing an N group to metal particles or metal compound particles, and further adding a surfactant and/or a chelating agent.

[39] The colloid solution according to [2], prepared by dissolving a metal compound in a solvent, causing the metal particles to precipitate, then adding a water-soluble high molecular weight dispersant containing an N group, and further adding a surfactant and/or a chelating agent.

[40] The colloid solution according to [2], prepared by dissolving a metal compound in a solvent, causing the metal particles to precipitate by reducing the metal compound, then adding a water-soluble high molecular weight dispersant containing an N group, and further adding a surfactant and/or a chelating agent.

[41] The colloid solution according to any of [1] to [40], used for confirming performance of a porous membrane by detecting the colloid particle permeation conditions through the porous membrane.

[42] The colloid solution according to any of [1] to [41], wherein the colloid particles have a particle diameter equivalent to the particle diameter of viruses, and the performance of the porous membrane to be confirmed is the performance relating to virus removal.

[43] The colloid solution according to any of [1] to [42], wherein the porous membrane is a virus removal membrane and the colloid solution is used as a solution containing viral substitute particles in an integrity test of the membrane.

[44] The colloid solution according to any of [1] to [43], which does not produce precipitate when stored at room temperature for one year and does not exhibit phase separation (solid/liquid separation).

In addition to the above-described inventions relating to colloid solutions, the following various inventions are included. The following descriptions in this specification relating to the above-described colloid solutions provide persons skilled in the art with a sufficient basis of understanding.

1. A method for producing a colloid solution comprising adding a water-soluble high molecular weight dispersant containing an N group to metal particles or metal compound particles, and further adding a surfactant and/or a chelating agent.

2. A method for producing a colloid solution comprising dissolving a metal compound in a solvent, causing the metal particles to precipitate, then adding a water-soluble high molecular weight dispersant containing an N group, and further adding a surfactant and/or a chelating agent.

3. The method for producing a colloid solution according to 1 or 2, comprising dissolving a metal compound in a solvent, causing the metal particles to precipitate by reducing the metal, then adding a water-soluble high molecular weight dispersant containing an N group, and further adding a surfactant and/or a chelating agent.

4. An adsorption preventive agent capable of preventing metal particles or metal compound particles in a colloid solution containing metal particles or metal compound particles from being adsorbed on the surface of a porous membrane, comprising (1) a water-soluble high molecular weight dispersant containing an N group and/or (2) a surfactant and/or a chelating agent as effective components.

5. An adsorption preventive agent capable of preventing metal particles or metal compound particles in a colloid solution containing metal particles or metal compound particles from being adsorbed on a porous membrane, comprising (1) a water-soluble high molecular weight dispersant containing an N group and/or (2) a surfactant and/or a chelating agent as effective components.

6. An adsorption preventive agent capable of preventing metal particles or metal compound particles in a colloid solution containing metal particles or metal compound particles from being adsorbed on a porous membrane, comprising (1) a water-soluble high molecular weight dispersant containing an N group and (2) a surfactant and/or a chelating agent as effective components.

7. An adsorption preventive agent capable of preventing metal particles or metal compound particles in a colloid solution containing metal particles or metal compound particles from being adsorbed on a porous membrane, comprising (1) a water-soluble high molecular weight dispersant containing an N group and (2) a surfactant as effective components.

8. An adsorption preventive agent capable of preventing metal particles or metal compound particles in a colloid solution from containing metal particles or metal compound particles being adsorbed on a porous membrane, comprising (1) a water-soluble high molecular weight dispersant containing an N group and (2) a chelating agent as effective components.

9. An adsorption preventive agent capable of preventing metal particles or metal compound particles in a colloid solution containing metal particles or metal compound particles from being adsorbed on a porous membrane, comprising (1) a water-soluble high molecular weight dispersant containing an N group and (2) a surfactant and a chelating agent as effective components.

10. An adsorption preventive agent capable of preventing metal particles or metal compound particles in a colloid solution containing metal particles or metal compound particles from being adsorbed on a porous membrane, comprising a water-soluble high molecular weight dispersant containing an N group as an effective component.

11. An adsorption preventive agent capable of preventing metal particles or metal compound particles in a colloid solution containing metal particles or metal compound particles from being adsorbed on a porous membrane, comprising a surfactant and/or a chelating agent as effective components.

12. An adsorption preventive agent capable of preventing metal particles or metal compound particles in a colloid solution containing metal particles or metal compound particles from being adsorbed on a porous membrane, comprising a surfactant as an effective component.

13. An adsorption preventive agent capable of preventing metal particles or metal compound particles in a colloid solution containing metal particles or metal compound particles from being adsorbed on a porous membrane, comprising a chelating agent as an effective component.

14. An adsorption preventive agent capable of preventing metal particles or metal compound particles in a colloid solution from being adsorbed on a porous membrane, in which the colloid solution contains at least (1) metal particles or metal compound particles having an average particle diameter of 1-100 nm, (2) a water-soluble high molecular weight dispersant containing an N group, and (3) water and/or a water-soluble organic solvent, and has the following properties (a) and (b):

(a) exhibiting a change in the maximum absorption wavelength in the range from −2.0 nm to +2.0 nm before and after being stored at room temperature for 180 days at a constant pH in a range from pH4 to pH11 and (b) exhibiting a change in the maximum absorption wavelength in the range from −2.0 nm to +2.0 nm before and after being stored at 50° C. for one year at pH5.

15. The adsorption preventive agent according to any of 4 to 14, wherein the porous membrane is a virus removal membrane.

16. The adsorption preventive agent according to any of 4 to 15, wherein the porous membrane is a cellulose membrane.

17. The adsorption preventive agent according to any of 8, 10, and 13 to 15, wherein the porous membrane is a synthetic polymer porous membrane and the colloid solution does not contain a surfactant.

18. An adsorption preventive method capable of preventing metal particles or metal compound particles in a colloid solution containing metal particles or metal compound particles from being absorbed on the surface of a porous membrane, comprising (1) a water-soluble high molecular weight dispersant containing an N group and/or (2) a surfactant and/or a chelating agent as effective components.

19. An adsorption preventive method capable of preventing metal particles or metal compound particles in a colloid solution containing metal particles or metal compound particles from being absorbed on a porous membrane, comprising (1) a water-soluble high molecular weight dispersant containing an N group and/or (2) a surfactant and/or a chelating agent as effective components.

20. An adsorption preventive method capable of preventing metal particles or metal compound particles in a colloid solution containing metal particles or metal compound particles from being absorbed on a porous membrane, the method comprising adding (1) a water-soluble high molecular weight dispersant containing an N group and (2) a chelating agent.

21. An adsorption preventive method capable of preventing metal particles or metal compound particles in a colloid solution containing metal particles or metal compound particles from being absorbed on a porous membrane, the method comprising adding (1) a water-soluble high molecular weight dispersant containing an N group and (2) a surfactant and a chelating agent.

22. An adsorption preventive method capable of preventing metal particles or metal compound particles in a colloid solution containing metal particles or metal compound particles from being absorbed on a porous membrane, the method comprising adding (2) a surfactant and/or a chelating agent after the addition of (1) a water-soluble high molecular weight dispersant containing an N group.

23. An adsorption preventive method capable of preventing metal particles or metal compound particles in a colloid solution containing metal particles or metal compound particles from being absorbed on a porous membrane, in which the colloid solution contains at least (1) metal particles or metal compound particles having an average particle diameter of 1-100 nm, (2) a water-soluble high molecular weight dispersant containing an N group and (3) water and/or a water-soluble organic solvent, and the colloid solution has the following properties (a) and (b):
  (a) exhibiting a change in the maximum absorption wavelength in the range from −2.0 nm to +2.0 nm before and after being stored at room temperature for 180 days at a constant pH in a range from pH4 to pH11 and
  (b) exhibiting a change in the maximum absorption wavelength in the range from −2.0 nm to +2.0 nm before and after being stored at 50° C. for one year at pH5.

24. The adsorption preventive method capable of preventing metal particles or metal compound particles in a colloid solution containing metal particles or metal compound particles from being absorbed on a porous membrane according any of 18 to 23, wherein the colloid solution contains (1) metal particles or metal compound particles having an average particle diameter of 1-100 nm, and at least any one of (2) the water-soluble high molecular weight dispersant containing an N group is poly(vinylpyrrolidone) or a poly(vinylpyrrolidone) copolymer, or (3) the surfactant is dodecylsulfuric acid or its salt or the chelating agent is at least one of tripolyphosphoric acid, polyacrylic acid, polyacrylic acid copolymer, ethylenediaminetetraacetic acid, or salts of these acids.

25. The adsorption preventive method according to any of 18 to 24, wherein the porous membrane is a virus removal membrane.

26. The adsorption preventive method according to any of 18 to 25, wherein the porous membrane is a cellulose membrane.

27. The adsorption preventive method according to any of 20 and 23 to 25, wherein the porous membrane is a synthetic polymer porous membrane and the colloid solution does not contain a surfactant.

28. A colloidal state maintenance agent for metal particles or metal compound particles, wherein the colloid solution contains at least (1) metal particles or metal compound particles having an average particle diameter of 1-100 nm,
  (2) a water-soluble high molecular weight dispersant containing an N group, and
  (3) water and/or a water-soluble organic solvent, and the colloidal state maintenance agent having the following properties (a) and (b):
  (a) exhibiting a change in the maximum absorption wavelength in the range from −2.0 nm to +2.0 nm before and after being stored at room temperature for 180 days at a constant pH in the range from pH4 to pH11 and
  (b) exhibiting a change in the maximum absorption wavelength in the range from −2.0 nm to +2.0 nm before and after being stored at 50° C. for one year at pH5.

29. A method for maintaining a colloidal state of metal particles or metal compound particles, wherein the colloid solution contains at least (1) metal particles or metal compound particles having an average particle diameter of 1-100 nm,
  (2) a water-soluble high molecular weight dispersant containing an N group and
  (3) water and/or a water-soluble organic solvent, and the method comprising providing the colloid solution with the following properties (a) and (b):
  (a) exhibiting a change in the maximum absorption wavelength in the range from −2.0 nm to +2.0 nm before and after being stored at room temperature for 180 days at a constant pH in a range from pH4 to pH11 and
  (b) exhibiting a change in the maximum absorption wavelength in the range from −2.0 nm to +2.0 nm before and after being stored at 50° C. for one year at pH5.

30. An integrity test method of a virus removal membrane comprising causing a colloid solution of metal particles or metal compound particles to be filtered through the virus removal membrane, in which the colloid solution contains at least (1) metal particles or metal compound particles having an average particle diameter of 1-100 nm, (2) a water-soluble high molecular weight dispersant containing an N group, and (3) water and/or a water-soluble organic solvent, and has the following properties (a) and (b):
  (a) exhibiting a change in the maximum absorption wavelength in the range from −2.0 nm to +2.0 nm before and after being stored at room temperature for 180 days at a constant pH in a range from pH4 to pH11 and
  (b) exhibiting a change in the maximum absorption wavelength in the range from −2.0 nm to +2.0 nm before and after being stored at 50° C. for one year at pH5.

31. The integrity test of a virus removal membrane according to 30, wherein a surfactant and/or a chelating agent are added to the colloid solution according to [1] immediately before the integrity test.

32. An integrity test of a virus removal membrane, comprising using a porous cellulose membrane as virus removal membrane, washing the used membrane with an alkali, then with water, and causing the membrane to come in contact with the colloid solution.

Effects of the Invention

The metal colloid solution of the present invention is expected to possess excellent storage stability, temperature stability, and pH stability. In addition, since the removability after filtering the metal colloid solution of the present invention through a virus removal membrane has a correlation with the virus removability, expansion of the pH range of a test solution during the test, reduction of test time (washing time), simplification of operation, and detection due to very small pore diameter difference in the virus removal membrane (high detection capability), all of which have been impossible in the integrity test of a virus removal membrane heretofore, are now possible.

In an integrity test using the gold colloid solution disclosed in JP-A-07-132215 and a virus removal membrane made from synthetic polymer such as polyvinylidene fluoride, of which the surface was hydrophilized, the gold colloid solution could not be filtered at all due to the effect of a surfactant contained in the solution. Thus, removability of the membrane could not be confirmed by the gold colloid filtration. Although the gold colloid solution not containing a surfactant could be filtered through the membrane, an accurate integrity test could not be completed due to adsorption of colloidal gold particles to the membrane material. Measurement of a porous membrane of synthetic polymer is now possible by using the colloid solution of the present invention.

BEST MODE FOR CARRYING OUT THE INVENTION

Figure 1:
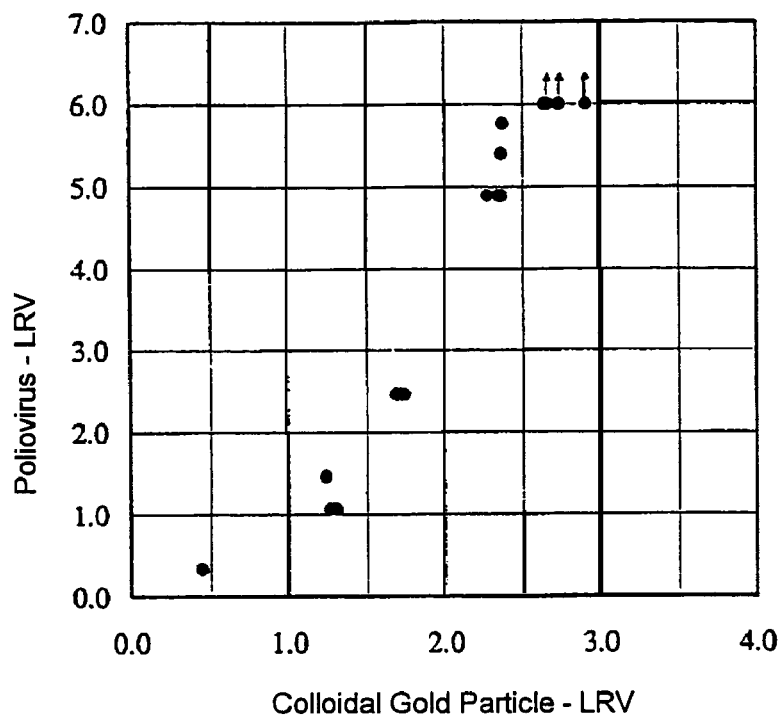
FIG. 1 is a diagram showing a correlation between removability of colloidal gold particles and removability of polioviruses. The arrow indicates that the LRV is larger than the indicated value. The horizontal axis indicates "colloidal gold particle LRV", whereas the vertical axis indicates "poliovirus LRV".

The present invention will now be explained in detail.

As an example of the metal colloid solution of the present invention, a metal colloid solution containing metal particles (or metal compound particles), a water-soluble high molecular weight dispersant containing an N group, and water and/or a water-soluble organic solvent can be given.

Of the metal particles and metal compound particles, metal particles are preferred.

As the metals forming the colloid particles, metals mentioned in the above invention [17] can be given. Noble metals, particularly gold, is preferable as the metal.

To use the colloid solution for in vitro diagnostic product or an integrity test of porous membrane, the colloid solution is preferably identified in the visible region. A colloid solution having maximum absorption wavelength in a visible region is particularly preferable. As the wavelength in a visible region, a wavelength from 350 to 650 nm is preferably used. When gold is used as metal particle, the color of the colloid solution is from red-purple to purple, although the color changes according to the particle diameter.

The metal particles and metal compound particles are preferably unreactive. Specifically, it is preferable that colloid particles itself do not chemically change, and/or colloid particles do not react with a porous membrane.

The average particle diameter of the metal particles or metal compound particles is preferably from 1 to 100 nm to ensure stable dispersion. A more preferable range is from 1 to 50 nm. The minimum diameter of the particles for practical use in the integrity test of virus removal membrane is usually 1 nm or more, preferably 5 nm or more, more preferably 10 nm or more, and particularly preferably 15 nm or more. To ensure stable dispersion, the maximum limit is usually 100 nm or less, preferably 75 nm or less, more preferably 50 nm or less, and particularly preferably 40 nm or less. In some case, 37 nm or less is ideal.

The diameter of the metal particles or metal compound particles contained in the metal colloid solution of the present invention is usually expressed by a circle-equivalent diameter. Specifically, a project area of a particle is calculated from a photograph observed through an electron microscope and the diameter of the particle is shown as the diameter of the circle having the same area The average particle diameter is expressed by the number average diameter of those circle-equivalent diameters.

In the integrity test of a virus removal membrane for removing small viruses with a diameter of 20-25 nm such as a parvovirus, the average particle diameter in the range of 15 to 25 nm is preferable. A more preferable range is from 15 to 22 nm. The removability when a metal colloid solution with an average diameter of 15-25 nm is filtered through a virus removal membrane for removing small viruses has a high correlation with the removability when small viruses such as a parvovirus are filtered through the removal membrane.

The percent of variation in particle diameter distribution of metal particles or metal compound particles is preferably 30% or less, more preferably 27% or less, and occasionally 26% or less, in order to use the metal colloid solution in an integrity test of virus removal membranes.

The percent of variation can be calculated according to the following formula.

[Percent of variation (%)=$\sigma$ (standard deviation)×100/ average particle diameter]

In order to use the metal colloid solution for the integrity test of porous membrane, the shape of the metal particles or metal compound particles is preferably isotropic or approximately isotropic and the ratio of major axis/minor axis of the particles is preferably from 1 to 2, and more preferably from 1 to 1.8, and particularly preferably from 1 to 1.7.

The amount of the metal particles or metal compound particles in the colloid solution is preferably in a range from 1 to 1,000 ppm, more preferably from 10 to 800 ppm, and still more preferably from 20 to 700 ppm. The amount of 1 ppm or more is preferable from the viewpoint of usability in integrity tests, with an amount of 10 ppm or more being more preferable, and 20 ppm or more being still more preferable. The upper limit is not particularly limited inasmuch as the dispersion stability and other conditions are not adversely affected. The amount is usually. 1,000 ppm or less, preferably 800 ppm or less, and still more preferably 700 ppm or less. In another amount expression, an amount from 0.0001 to 0.1 wt % is given as a preferable range. The lower limit of the amount is usually 0.0001 wt % or more, preferably 0.001 wt % or more, and still more preferably 0.002 wt % or more. The upper limit is not particularly limited. However, the amount is usually 0.1 wt % or less, preferably 0.08 wt % or less, and still more preferably 0.07 wt % or less.

The water-soluble high molecular weight dispersant containing an N group of the present invention is preferably a compound exhibiting affinity with metal particles or metal compound particles, and also exhibiting affinity with solvents (solvation). The N group is preferably a group containing a pyrrolidone group. At least one or more polymers selected from poly(vinylpyrrolidone), N-vinylpyrrolidone/styrene copolymer, N-vinylpyrrolidone/vinyl-acetate copolymer, and the like can be given as preferable examples. The water-soluble high molecular weight dispersant containing an N group exhibits direct protective colloidal action on a metal colloid or metal compound colloid and is expected to prevent aggregation of colloid particles, maintain constant surface conditions (electric potential), and prevent colloid particles from being adsorbed to other substances. The water-soluble high molecular weight dispersant containing an N group is also expected to maintain stability of the colloid solution against environmental changes (temperature, pH).

Although not specifically limited, the molecular weight of the water-soluble high molecular weight dispersant containing an N group is usually in the range from 1,000 to 2,000,000, more preferably from 1,000 to 100,000, and till more preferably from 1,000 to 50,000. The lower limit of the molecular weight is usually 1,000 or more, preferably 2,000 or more, still more preferably 5,000 or more, and particularly preferably 7,000 or more from the viewpoint of ensuring stability of metal or metal compound colloidal dispersion. The upper limit of the molecular weight is usually 2,000,000 or less, preferably 1,000,000 or less, more preferably 100,000 or less, and particularly 50,000 or less from the viewpoint of ensuring viscosity, solubility in solvents, handling easiness, effect on colloidal particle size of metal or metal compound, and dispersion stability.

The amount of the water-soluble high molecular weight dispersant containing an N group to be added is usually from 0.001 to 10 wt %, preferably from 0.01 to 5 wt %, and more preferably from 0.1 to 5 wt %. From the viewpoint of ensuring dispersion stability, the lower limit of the amount of addition is usually 0.001 wt % or more, preferably 0.01 wt % or more, more preferably 0.05 wt % or more, and particularly preferably 0.1 wt % or more. From the viewpoint of viscosity, solubility in solvents, and handling easiness, the upper limit is usually 10 wt % or less, preferably 7.5 wt % or less, and more preferably 5 wt % or less, and particularly preferably 3 wt % or less.

The colloid solution of the present invention may further comprise one or more types of surfactants and/or chelating agents. The surfactant and/or chelating agent is expected to exhibit, for example, the effect of increasing dispersion stability and the effect of controlling the metal colloid solution from being absorbed in the material of membrane.

As the surfactants, anionic surfactants or nonionic surfactants can be used. As examples of the anionic surfactant, dodecylsulfuric acid and its salts can be given. Any types of salts, for example, commercially available lithium salt and sodium salt, can be used. Sodium dodecyl sulfate can be given as a preferable example of the salt. As the nonionic surfactant, Triton X-100, Tween 20, Tween 80, and the like can be used.

As examples of the chelating agent used in the present invention, at least one of tripolyphosphoric acid, polyacrylic acid, polyacrylic acid copolymer, ethylenediaminetetraacetic acid, or salts thereof can be given, with sodium polyacrylate and polyacrylic acid copolymer being preferable. Any types of salts can be used. As preferable examples, commercially available sodium salt or potassium salt can be given. Preferably, at least one of sodium tripolyphosphate, sodium polyacrylate, sodium polyacrylate copolymer, and sodium ethylenediaminetetraacetate (particularly preferably disodium ethylenediaminetetraacetate) can be given.

The amount of surfactant and/or chelating agent in the colloid solution, in terms of the weight of compounds, is preferably from 0.001 to 5.0 wt %. The amount from 0.001 to 7.0 wt % is also preferable. Although not specifically limited inasmuch as the effect of the present invention (such as the capability of controlling adsorption to the membrane material) can be exhibited, the lower limit of the amount is usually 0.001 wt % or more, preferably 0.005 wt % or more, more preferably 0.01 wt % or more, still more preferably 0.05 wt % or more, and particularly preferably 0.1 wt % or more. In some cases, the lower limit of 0.2 wt % or more, or even 0.5 wt % or more, is preferable. Although not specifically limited inasmuch as the effects of the present invention such as viscosity, solubility in solvents, preventing aggregation of colloid particles, and the like are not adversely affected, the upper limit is usually 7 wt % or less, preferably 5.0 wt % or less, more preferably 4.0 wt % or less, still more preferably 3.0 wt % or less, and particularly preferably 2.5 wt % or less. In some cases, the upper limit is preferably 2.0 wt % or less, more preferably 1.0 wt % or less, still more preferably 0.5 wt % or less, and particularly preferably 0.3 wt % or less.

More preferable amounts of the surfactant and the chelating agent are respectively as follows.

As the amount of the surfactant of the present invention, a more preferable range of 0.01 to 3 wt %, and still more preferable range of 0.05 to 2.0 wt %, can be given, for example. Although not specifically limited inasmuch as the effect of the present invention (such as the capability of controlling adsorption to the membrane material) can be exhibited, the lower limit of the surfactant amount is usually 0.001 wt % or more, preferably 0.005 wt % or more, more preferably 0.01 wt % or more, still more preferably 0.05 wt % or more, and particularly preferably 0.1 wt % or more. The upper limit is not also specifically limited inasmuch as the effects of the present invention such as solubility in solvents and other conditions are not adversely affected. For example, the upper limit is usually 5 wt % or less, preferably 3.0 wt % or less, more preferably 2.5 wt % or less, still more preferably 2.0 wt % or less, particularly preferably 1.0 wt % or less, and in some cases 0.5 wt % or less.

Although not specifically limited inasmuch as the effect of the present invention (such as the capability of controlling adsorption to the membrane material and the like) can be exhibited, the amount of the lower limit of the chelating agent used in the present invention is usually 0.05 wt % or more, preferably 0.1 wt % or more, more preferably 0.2 wt % or more, still more preferably 0.3 wt % or more, and particularly preferably 0.5 wt % or more. The upper limit also is not specifically limited in as much as the effects of the present invention such as viscosity, solubility in solvents, and ease of handling are not adversely affected and there are no other disadvantages such as crosslinking or aggregation of metal or metal compound colloid particles. Such a limit is usually 7.0 wt % or less, preferably 5.0 wt % or less, more preferably 4.0 wt % or less, and still more preferably 3.0 wt % or less. In some case, the upper limit may be 2.5 wt % or less, preferably 2.0 wt % or less, more preferably 1.5 wt % or less, and still more preferably 1.0 wt % or less.

The molecular weight of sodium polyacrylate and polyacrylic acid copolymer used in the present invention is usually from 100 to 10,000, for example. Although the lower limit of the molecular weight of the sodium polyacrylate and polyacrylic acid copolymer is not specifically limited inasmuch as the effect of the present invention (such as an adsorption inhibiting effect) can be exhibited, the molecular weight is usually 100 or more, preferably 500 or more, still more preferably 1,000 or more, and particularly preferably 5,000 or more. Although not specifically limited inasmuch as the effects of the present invention such as viscosity, solubility in solvents, ease of handling, and other conditions are not adversely affected, the upper limit is usually 10,000 or less, preferably 9,000 or less, more preferably 8,000 or less, and particularly preferably 7,000 or less.

In the colloid solution of the present invention, both a surfactant and a chelating agent may be used in combination, if required, or it is also possible to use either one of the surfactant and chelating agent. The use of a chelating agent in addition to a surfactant is expected to provide effects that dispersion stability is improved and adsorption of colloid particles to the material of membrane is inhibited, for example. In addition, the colloid solution may further include an organic acid and its salt. As examples of the organic acid and its salt, citric acid, sodium citrate, and the like can be given.

As an example of using the surfactant and/or chelating agent in a colloid solution used in the integrity test of a virus removal membrane, when the material of the membrane is cellulose, either a surfactant or a chelating agent, or both in combination can be used. When a membrane made from a synthetic polymer is used, a surfactant may not be used, but a chelating agent alone is used.

The water-soluble high molecular weight dispersant containing an N group in the present invention has function to protect colloid and stabilize dispersion, and is expected further to increase the stability effect by addition of the surfactant and/or chelating agent. The water-soluble high molecular weight dispersant containing an N group also controls adsorption of colloid particles to other materials. This effect of adsorption control is expected to be improved by addition of the surfactant and/or chelating agent. As a result, adsorption of colloid particles to other materials, for example, a container for storing the colloid solution for a long time, as well as to porous membrane, is expected to be controlled.

The colloid solution of the present invention can be prepared by the following methods, for example. Specifically, a method of adding a water-soluble high molecular weight dispersant containing an N group to metal particles or metal compound particles, and further adding a surfactant and/or a chelating agent can be given. It is possible to add the water-soluble high molecular weight dispersant containing an N group, after dissolving a metal compound in a solvent and causing the metal particles to form, and then further to add a surfactant and/or a chelating agent. Taking the case in which metal particles are used as an example, the metal colloid solution used in the present invention can be prepared by dissolving a raw material metal compound in a solvent and reducing into metal, thereby obtaining particles. As examples of the metal compound used as a raw material, chloroauric acid, silver nitrate, chloroplatinic acid, rhodium chloride (III), palladium chloride (II), ruthenium chloride (III), chloroiridate, osmium oxide (VII), and the like can be given. As the reducing agent, citric acid, sodium citrate, tannic acid, hydrazine, sodium boronhydride, and the like can be given. Although not specifically limited, the reaction temperature may be in the range from room temperature to the boiling point of the solvent, preferably from 25 to 100° C., and more preferably from 40 to 100° C. There are also no specific limitations to the reaction time, which may be from several minutes to several days, for example. In the case of metal compound particles, the particles can be obtained according to the method disclosed in JP-A-08-141388. After obtaining the metal particles or metal compound particles, a prescribed amount of water-soluble high molecular weight dispersant containing an N group is added to produce a colloid solution. After that, a surfactant and/or chelating agent are further added, if required. In addition, an organic acid and its salt may further be added.

As the solvent for the metal compound used as the raw material of the present invention or the dispersion medium for the colloid solution, water, a water-soluble organic solvent, or a mixture thereof is preferably used. As examples of the water-soluble organic solvent, ethanol, methanol, ethylene glycol, and the like can be given. Preferably, water, ethanol, methanol, and a mixture thereof can be given, and water is particularly preferable.

The viscosity at 25° C. of the colloid solution of the present invention is preferably from 0.8 to 5 cP (mPa·s). A more preferable range is from 0.8 to 2 cP (mPa·s), for example. Though the lower limit of the viscosity of the colloid solution is not specifically limited inasmuch as the effect of the present invention is exhibited, the lower limit is usually 0.8 cP. The upper limit is not particularly limited inasmuch as ease of handling, operation time when a fluid is processed by the membrane, and other conditions are not adversely affected. The viscosity is usually 5 cP or less, and preferably 2 cP or less, for example. More preferably, the viscosity is 1.7 cP or less, with 1.5 cP or less viscosity being particularly preferable.

In evaluating the stability of the metal colloid solution in the present invention, storage stability, temperature stability, and pH stability can be evaluated by measuring optical characteristics or by inspecting production of aggregate, formation of precipitate, and the like by observation. Stability against salts can be confirmed by salting-out and the like.

As the method for measuring optical characteristics, measurement of the maximum absorption wavelength of the metal colloid solution using a spectrophotometer can be given, for example. As the method for measuring the maximum absorption wavelength of the colloid solution, a method of scanning by light with a wavelength in the range in which the absorbance wavelength inherent to colloid particles can be identified (preferably visible region, i.e. the range from 350 to 650 nm) using a spectrophotometer and determining the wavelength at which the absorption is maximum in the resulting absorption spectrum can be given, for example. As the spectrophotometer, an apparatus capable of measuring from the visible wavelength region to the ultraviolet wavelength region such as a ultraviolet-visible region spectrophotometer "UV-160A" manufactured by Shimadzu Corp., for example, can be used. The maximum absorption wavelength represents the average particle diameter of metal colloid particles.

Storage stability in the present invention, indicated by, for example, the change in maximum absorption wavelength when the colloid solution has been stored at 50° C. for at least 90 days, and preferably for one year, from the initial day (day 0), is preferably in the range from −2.0 nm to +2.0 nm. The difference is preferably in the range from −1.7 nm to +1.7 nm, more preferably from −1.5 nm to +1.5 nm, and still more preferably from −1 nm to +1 nm. In some cases, the range is preferably from −1.6 nm to +1.6 nm, and more preferably from −1.3 nm to +1.3 nm. The stability can also be confirmed by production of aggregate or precipitate by observation.

The following formula that indicates the rate of change (RC) of the maximum absorption wavelength can also be used to evaluate storage stability.

RC of maximum absorption wavelength (%)=(difference between the maximum absorption wavelength during transitional period to a specific day and the maximum absorption wavelength of day 0 (nm)×100)/maximum absorption wavelength on day 0 (nm)

The RC of maximum absorption wavelength of the colloid solution stored for the same number of days under the same conditions as described above is usually in the range from −0.38% to +0.38%, preferably from −0.32% to +0.32%, more preferably from −0.28% to +0.28%, and still more preferably from −0.19% to +0.19%. In some cases, the range is preferably from −0.30% to +0.30%, and more preferably from −0.24% to +0.24%.

In the storage stability in the present invention, the colloid solution is also expected to exhibit a preferable property that precipitate does not produced when allowed to stand at 80° C. and at pH5 for 6 days, for example. In addition to the judgment of non-production of precipitate, change in maximum absorption wavelength can also be used. It is preferable that both the difference from the maximum absorption wavelength on day 0 and the RC of the maximum absorption wavelength are in the above ranges.

In regard to pH stability in the present invention, the difference of maximum absorption wavelength, when the colloid solution has been stored at a prescribed pH in the range from pH4 to pH11 at room temperature for 180 days, from the maximum absorption wavelength on the initial day (day 0) is preferably in the range from −2.0 nm to +2.0 nm. The difference is preferably in the range from −1.7 nm to +1.7 nm, more preferably from −1.5 nm to +1.5 nm, and still more preferably from −1 nm to +1 m. In some cases, the range is preferably from −1.6 nm to +1.6 nm, and more preferably from −1.3 nm to +1.3. In addition to the stability during storage at room temperature for the above-mentioned period of 180 days, the above ranges of the change of maximum absorption wavelength (difference from the maximum absorption wavelength on day 0) is preferably satisfied at room temperature for 200 days, more preferably for 300 days, and particularly preferably for 360 days. The preferable range indicated as the above RC of maximum absorption wavelength is usually in the range from −0.38% to +0.38%, preferably from −0.32% to +0.32%, more preferably from −0.28% to +0.28%, and still more preferably from −0.19% to +0.19%. In some cases, the range is preferably from −0.30% to +0.30%, and more preferably from −0.24% to +0.24%.

The colloid solution of the present invention is also expected to possess storage stability to the extent that even the colloid solution with a high salt concentration does not exhibit any special change such as production of precipitate and the like. Preferably, a colloid solution (pH5) containing PVP does not produce precipitate when allowed to stand overnight after the addition of at least 0.2M of $CaCl_2$. Whether or not precipitate was produced can be confirmed by solid-liquid separation of the colloid solution.

In the present invention, the recovery rate of colloid particles can be determined by the following colloid collection test. Specifically, the colloid recovery rate is measured when the colloid solution to be evaluated is filtered through a collection test porous membrane. A collection test porous membrane that satisfies the following inequality formula, is preferably used.

(average pore diameter (nm) of the collection test porous membrane)−(average particle diameter (nm) of colloid)>10 nm The colloid recovery rate is expressed as the ratio of the colloid concentration before filtration and the colloid concentration after filtration by the following formula.

Colloid recovery rate (%)=(Cf/Co)×100 wherein Co is absorbance before filtration and Cf is absorbance after filtration.

When the colloid solution is used for the integrity test of a virus removal membrane, the porous membrane for the collection test is preferably made from the same material as the virus removal membrane. A high recovery rate is usually judged to indicate a small adsorption force of colloid particles to the material of the membrane. As a result, the performance can be evaluated based on the principle of sieving particle depending on the pore diameter of the virus removal membrane, indicating appropriateness for the integrity test of the virus removal membrane. The recovery rate is usually 70% or more, preferably 75% or more, still more preferably 78% or more, and particularly preferably 80% or more. In some cases, 83% or more, preferably 94% or more, and particularly preferably 97% or more can be given as examples of preferable ranges.

More specifically, a metal colloid solution with an average particle diameter of 17 nm is filtered through a collection test porous membrane with an average pore diameter of about 35 nm, for example, and the concentrations of colloidal metal particles before and after filtration are compared. Any filtration method can be employed inasmuch as the method is optimal for each membrane, and a constant pressure dead-end method is given as an example. In so doing, a most appropriate filtration pressure range (in which the membrane structure is not broken) can be determined depending on the pressure resistance of each membrane. It is desirable to measure the recovery rate when a fluid is caused to pass through the membrane at a rate of 2.5 to 5.0 $l/m^2$.

The concentration of the metal colloid solution is measured by the following methods, for example. The absorption spectrum of the metal colloid solution is measured using a spectrophotometer or the like to identify the maximum absorption wavelength. The absorbance of the metal colloid solution at the maximum absorption wavelength is measured before and after filtration.

Cellulose or synthetic polymer can be given as particularly preferable material for the porous membrane used in the present invention.

As examples of the cellulose, regenerated cellulose, natural cellulose, and cellulose acetate can be given.

Thermoplastic polymers can be given as examples of the synthetic polymer used in the present invention. Preferable examples include polyvinylidene fluoride and polyether sulfone. It is preferable for the surfaces of polyvinylidene fluoride and polyether sulfone to be treated for providing hydrophilic properties. As a treatment for providing hydrophilic properties on a surface, a treatment for providing the surfaces of the membrane or surfaces of pores with properties of becoming spontaneously wetted with water can be given. Such a treatment is carried out according to a conventional method such as grafting or coating.

The integrity test of the present invention using viral substitute particles is highly reliable since the principle of the method is particle sieving filtration which is the same as the virus removal and, therefore, can obtain correlation of characteristics of the same type of mechanisms as the virus removal. In addition, the method of filtering colloidal gold is advantageous due to easy preparation of the colloid solution and simple, and accurate concentration measurement. In the integrity test, after the membrane has been used as a virus removal membrane, a step of washing the membrane is thought to be necessary for reducing the effect of the residues (e.g. protein, lipids, etc.) in the membrane on the measurement (such as change in the pore diameter distribution due to clogging of residues) to the maximum extent possible. After that, the colloid solution is filtered to confirm the removability (performance).of the virus removal membrane. Since the colloid solution of the present invention possesses high stability against pH change and is stable at a high salt concentration, the washing treatment of the colloid solution can be simplified.

As the average pore diameter of the virus removal membrane of the present invention, the range from 10 to 100 nm can be given as an example.

A conventional method can be applied to the integrity test using the colloid solution of the present invention. Specifically, the virus removal membrane after filtration is washed using a washing fluid such as a protein removing agent containing an acid, alkali, surfactant, and the like. After this, an alkali solution which remains in the membrane is neutralized with an acid or washed with water, following which the colloid solution is filtered through the washed virus removal membrane to measured the removability. Because the colloid solution of the present invention possesses stability in a wide pH range, the colloid solution has an advantage of appropriately selecting the pH according to the pH resistance of the virus removal membrane.

For example, in the integrity test of virus removal membrane made from regenerated cellulose using the colloid solution of the present invention, a membrane that has been used as a virus removal membrane can be washed with an alkali, then with water without washing with an acid to bring the pH of the fluid in the membrane to neutral region strictly, following which the membrane performance can be confirmed using the colloid solution.

In the integrity test of the virus removal membrane made from a synthetic polymer such as hydrophilized polyvinylidene fluoride using the colloid solution of the present invention, for example, a membrane that has been used as a virus removal membrane can be washed with an acid, then with water, following which the membrane performance can be confirmed using the colloid solution.

Any common method of washing can be used in the present invention without specific limitations. For example, ultrasonic washing in a washing fluid, dipping in a washing fluid, orderly washing, reverse washing, and the like may be used. Orderly washing herein is referred as a method of washing to cause a washing fluid in the same direction as the direction of the organic substance to be filtered, and reverse washing is referred as a method of washing to cause a washing fluid in the reverse direction to the direction of the organic substance to be filtered. Although selection depends upon the shape of the membrane, using the orderly washing and reverse washing is more effective.

Although the washing temperature in the present invention is not specifically limited inasmuch as there is no adverse effect on the washing fluid, the range from 4° C. to 40° C. is preferable.

Although the washing pressure in the present invention is not specifically limited inasmuch as there is no adverse effect on the structure of the porous membrane, a pressure of 100 kPa or less is used in the case of a cellulose membrane with low pressure resistance, and 300 kPa or less in the case of a polyvinylidene fluoride membrane and polysulfone membrane, it is preferable to use a pressure as high as possible.

As the method for confirming the performance of virus removal membrane, the following method of calculating the logarithmic reduction value (LRV) can be given. Specifically, although any method for filtering the colloid solution through the virus removal membrane may be employed inasmuch as the method is optimal for each membrane, a constant pressure dead-end method is given as an example. In this instance, although the pressure is not specifically limited inasmuch as there is no adverse effect on the structure of the porous membrane, a pressure of 100 kPa or less is used in the case of a cellulose membrane with low pressure resistance, and 300 kPa or less in the case of a polyvinylidene fluoride membrane and polysulfone membrane, it is preferable to use a pressure as high as possible.

The absorption spectrum of the metal colloid solution is measured using a spectrophotometer or the like to identify the maximum absorption wavelength. The absorbance of the metal colloid solution at the maximum absorption wavelength is measured before and after filtration and the resulting value is expressed as the logarithmic reduction value (LRV), which is calculated according to the following formula:

$$\text{Logarithmic reduction value } (LRV) = \text{Log}_{10}(Co/Cf)$$

wherein Co is the absorbance before filtration and Cf is the absorbance after filtration.

As types of the colloid solution of the present invention, a one-reagent type containing all components, a two-reagent type in which reagents are provided separately, and the like can be given. Specifically, a one-reagent type contains all of the metal particles or metal compound particles, an adsorption preventive agent which comprises a water-soluble high molecular weight dispersant containing an N group, a surfactant and/or a chelating agent; and a two-reagent type contains a colloid of metal particles or metal compound particles, and an adsorption preventive agent which comprises a water soluble high molecular weight dispersant containing an N group, a surfactant and/or a chelating agent; and the like. The reagents may contain the components either at concentrations prescribed for use in measurement or concentrations several times to 10 times of those concentrations.

The surfactant and/or the chelating agent may be added immediately before the step of causing the colloid solution to come into contact with a porous membrane (for example, an integrity test), may be added at the time of starting storage of the colloid or any optional time during storage, or may be added separately and intermittently. When intermittently added, either the surfactant and chelating agent may be separately added or the ultimate total amount of the surfactant and chelating agent may be divided and added in portions, respectively. The amount of the surfactant and chelating agent may be appropriately determined so that their ultimate concentrations in the colloid solution may be the above-described optimum concentrations.

As another preferable application of the colloid solution of the present invention, in vitro diagnostic can be given. The other potential applications include a photochromic material, antibacterial material, anti-fungal material, anti-alga material, magnetic material, non-linear optical material, pigment, catalyst, conductive material, and the like.

EXAMPLES

The present invention will now be described by way of examples and comparative examples, which should not be construed as limiting the present invention.

Example 1

80 g of a 6.0 mM chloroauric acid (manufactured by Wako Pure Chemical Industries, Ltd., guaranteed reagent) aqueous solution was put into in a reaction vessel. 320 g of distilled water and 13.1 g of a 4% sodium citrate aqueous solution were added and the mixture was reacted at 78° C. for 30 minutes. The concentration of gold in the solution was about 500 ppm. After completion of the reaction, 39.8 g of a 30% solution of PVP ("K-15" manufactured by Tokyo Kasei Kogyo Co., Ltd., molecular weight: 10,000) was added, followed by the addition of 24.0 g of a 5% sodium dodecylsulfate aqueous solution to obtain a concentrated purple blue solution of gold colloid solution. The solution was then adjusted to pH4.7 to pH5.3 using hydrochloric acid or sodium hydroxide. The gold colloid solution was dried on a mesh with a collodion membrane attached thereto to observe the dried colloid using a transmission electron microscope. Dispersion conditions of gold particles were excellent and the average particle diameter of the gold particles was about 28-37 nm. An absorption spectrum measured by a spectrophotometer to confirm the maximum absorption originating from gold plasmon at 520-530 nm. The spectrum originating from gold plasmon absorption may be seen in nano-particles with a particle size in the range from several nm to several tens of nm. In addition, it is known that there is a very high correlation between the value of the maximum absorption wavelength and the average particle diameter. The change in the maximum absorption wavelength of this gold colloid solution was observed to confirm that the difference of the maximum absorption wavelengths on the first day (day 0) and during each lapsed days after day 0 was from −1.5 nm to +1.5 nm (mostly from −1.0 nm to +1.0 nm). The gold colloid solution was stable for one year under the environment of 50° C. The results are shown in Table 1.

Example 2

The gold colloid solution prepared by the method of Example 1 was stored under an environment of 80° C. The absorption characteristics of the gold colloid solution were stable for a period of six days or more. The results are shown in Table 2.

Example 3

80 g of a 6.0 mM chloroauric acid aqueous solution was put into a reaction vessel. 320 g of distilled water and 15.9 g of a 4% sodium citrate aqueous solution were added and the mixture was reacted at 70° C. for 60 minutes. The concentration of gold in the solution was about 500 ppm. After completion of the reaction, 39.8 g of a 30% solution of PVP ("K-15" manufactured by Tokyo Kasei Kogyo Co., Ltd., molecular weight: 10,000) was added, followed by the addition of 24.0 g of a 5% sodium dodecylsulfate aqueous solution to obtain a concentrated vivid red solution of gold colloid. Solutions at pH2.0, pH3.0, pH4.0, pH5.0, pH7.0, pH9.0, and pH11.0 were prepared using hydrochloric acid or sodium hydroxide. These gold colloid solutions were dried on a mesh with a collodion membrane attached thereto to observe the dried gold colloid particles using a transmission electron microscope. Dispersion conditions of gold colloid particles were excellent and the average particle diameter of the gold particles was about 20 to 24 nm. Al gold colloid solutions with pH2 to pH11 were stored at room temperature for 180 days to confirm stable absorption characteristics. The results are shown in Table 3.

Example 4

Calcium chloride was added to the gold colloid solution prepared in Example 3. After sufficiently stirring, the colloid solution was allowed to stand overnight. The results are shown in Table 4.

The gold colloid solutions at pH4.0, pH5.0, pH7.0, pH9.0, and pH11.0 did not produce precipitate when calcium chloride was added up to the concentration of 0.2 M.

Comparative Example 1

80 g of a 6.0 mM chloroauric acid aqueous solution was put into a reaction vessel. 320 g of distilled water and 13.9 g of a 4% citric acid aqueous solution were added and the mixture was reacted at 80° C. for 30 minutes. The concentration of gold in the solution was about 500 ppm. After completion of the reaction, 18.0 g of a 20% polyethylene glycol solution manufactured by Sigma Co. was added, followed by the addition of 25.0 g of a 5% sodium dodecylsulfate aqueous solution manufactured by Nacalai Tesque, Inc. to. obtain a gold colloid solution. The solution was adjusted to pH4.7 to pH5.3 using hydrochloric acid or sodium hydroxide. The gold colloid solution was dried on a mesh with a collodion membrane attached thereto to observe the dried gold colloid particles using a transmission electron microscope. Dispersion conditions of gold particles were excellent and the average particle diameter of the gold particles was about 34-39 nm. The gold colloid solution was stored under the environment of 50° C. in the same manner as in Example 1. The results are shown in Table 1.

The stability of the gold colloid solution was found to be worse than the colloid solution of Example 1 and exhibited significant change in absorption characteristics after storage for 240 days.

Comparative Example 2

The gold colloid solution prepared in Comparative Example 1 was stored under an environment of 80° C. in the same manner as in Example. The results are shown in Table 2.

The stability of the gold colloid solution was found to be significantly worse in comparison with the colloid solution of Example 1. After storage for 4 days, the colloid solution produced aggregate and precipitation, and exhibited significant change in absorption characteristics.

Comparative Example 3

80 g of a 6.0 mM chloroauric acid aqueous solution was put into a reaction vessel. 320 g of distilled water and 15.9 g of a 4% citric acid aqueous solution were added and the mixture was reacted at 70° C. for 60 minutes. The concentration of gold in the solution was about 500 ppm. After completion of the reaction, 18.0 g of a 20% polyethylene glycol solution manufactured by Sigma Co. was added, followed by the addition of 25.0 g of a 5% sodium dodecylsulfate aqueous solution manufactured by Nacalai Tesque, Inc. to obtain a gold colloid solution. Solutions at pH2.0, pH3.0, pH4.0, pH5.0, pH7.0, pH9.0, and pH11.0 were prepared from this gold colloid solution using hydrochloric acid or sodium hydroxide. Among these, a colloid solution with pH5 was dried on a mesh with a collodion membrane attached thereto to observe the dried colloid using a transmission electron microscope. Dispersion conditions of gold particles were excellent and the average particle diameter of the gold particles was about 18-22 nm. The above gold colloid solutions with different pHs were stored at room temperature. The results are shown in Table 3. The solutions with a pH2.0, pH7.0, pH9.0, and pH11.0 were found to have poor storage stability as compared with the solution of Example 3. After storage for 180 days, the colloid solutions exhibited a change in absorption characteristics. After 90 days, absorption of the solution with a pH2.0 could not be measured due to production of aggregate and precipitate.

Comparative Example 4

Calcium chloride was added to the gold colloid solution prepared in Comparative Example 3. The resulting colloid solution was stirred and allowed to stand in the same manner as in Example 4. The results are shown in Table 4.

The gold colloid solution produced a large amount of aggregate and precipitate at a low concentration of 0.04 M or less.

Example 5

According to the method described in JP-A-04-371221, filters each having a membrane area of 0.01 m$^2$, were prepared from cuprammonium regenerated cellulose porous hollow fiber membranes with average pore diameter of 13.8 nm, 15.5 nm, 15.7 nm, 17.6 nm, 19.3 nm, 23.8 nm, 24.3 nm, 24.8 nm, and 36.1 nm. The average pore diameter of the obtained regenerated cellulose porous hollow fiber membrane was calculated according to the method described in the formula 2 in JP-A-04-371221. The gold colloid solutions at pH4 to pH11 of Example 3 were diluted to a gold colloid concentration of one-tenth using 0.27% sodium dodecylsulfate aqueous solutions at the same pHs and filtered through the above filters with different diameters. As a filtration method, the constant-pressure dead-end method was conducted under a filtration pressure of 26.7 kPa. The gold colloid concentration of 5 to 10 ml filtrate fractions was measured from the absorbance to calculate LRV of the gold colloid. Poliovirus used as an indicator virus was added to D-MEM containing 10% fetal bovine serum to prepare the solution with a concentration of $10^{6.47}$ TCID$_{50}$/ml. The resulting solution was then filtered through the above filter made from the hollow fiber membranes with different pore diameters. The virus concentration of 0 to 30 ml filtrate fractions was calculated as TCID$_{50}$/ml from the 50% cytopathic effect to FL cells. FIG. 1 shows the correlation between removability of gold colloid and removability of virus.

The removability of gold colloid and removability of virus showed a good correlation. As a result, the metal colloid solution of the present invention was confirmed to be applicable to the integrity test of a virus removal membrane.

Example 6

According to the method described in JP-A-04-371221, a filter with a membrane area of 0.001 m$^2$ was prepared from a cuprammonium regenerated cellulose porous hollow fiber membrane with an average pore diameter of 16.5 nm. The gold colloid solutions with different pHs prepared in Example 3 were diluted to a gold colloid concentration of one-tenth using 0.27% sodium dodecylsulfate aqueous solutions and filtered using the constant-pressure dead-end method under a filtration pressure of 26.7 kPa. The gold colloid concentration of 4 to 6 ml filtrate fractions was determined by absorbance measurement to calculate the LRV. The results are shown in Table 5.

The gold colloid removability showed a value of almost LRV=2 in the range of pH4 to pH11, indicating that the integrity test will results in a constant LRV value in this pH range.

Comparative Example 5

The gold colloid solutions with different pHs prepared in Comparative Example 3 were diluted in the same manner as in Example 6 and filtered using the same filter as in Examples 6 to calculate the LRV. The results are shown in Table 5.

The LRV value was found to increase as the pH increases, indicating dependency of the LRV on pH.

Example 7

80 g of a 6.0 mM chloroauric acid aqueous solution was put into a reaction vessel. 320 g of distilled water and 19.0 g of a 4% sodium citrate aqueous solution were added and the mixture was reacted at 70° C. for 60 minutes. The concentration of gold in the solution was about 500 ppm. After completion of the reaction, 39.8 g of a 30% PVP (manufactured by Tokyo Kasei Kogyo Co., Ltd., molecular weight: 10,000) solution was added, followed by the addition of 24.0 g of a 5% sodium dodecylsulfate aqueous solution to obtain a concentrated vivid red solution of gold colloid. The solution was adjusted to pH4.7 to pH5.3 using hydrochloric acid or sodium hydroxide. These gold colloid solutions were dried on a mesh with a collodion membrane attached thereto, followed by observing the dried gold colloid particles using a transmission electron microscope. Dispersion conditions of gold colloid particles were excellent and the average particle diameter of the gold particles was about 16-20 nm. According to the method described in JP-A-04-371221, a filter with a membrane area of 0.01 m$^2$ was prepared from a cuprammonium regenerated cellulose porous hollow fiber membrane with an average pore diameter of 19.3 nm. After filtering a 3% bovine globulin saline solution for one hour, the filter was washed with 30 ml of water, 30 ml of a mixture of 0.25 N NaOH and 1% SDS, 80 ml of ⅓,₀₀₀ N HCl, and 30 ml of water. The gold colloid solution was diluted to a gold colloid concentration of one-tenth using a 0.27% sodium dodecylsulfate aqueous solution and filtered under a filtration pressure of 26.7 kPa. The gold colloid concentration of 5 to 10 ml filtrate fraction was determined by absorbance measurement to calculate the LRV. The gold colloid was filtered using same procedure as above except for omission of the HCl washing step and the LRV was calculated. For comparison, the gold colloid was filtered using a filter for which globulin filtration and the washing process were omitted, and the LRV was calculated. The water permeation recovery rate is a rate of the water permeation amount of the filter after a protein washing process to the water permeation amount before protein filtration. The results are shown in Table 6.

The gold colloid removability of the filter for which the HCl washing step was omitted showed the same LRV as the washed filter.

Example 8

80 g of a 6.0 mM chloroauric acid aqueous solution was put into a reaction vessel. 320 g of distilled water and 19.4 g of a 4% sodium citrate aqueous solution were added and the mixture was reacted at 70° C. for 60 minutes. The concentration of gold in the solution was about 500 ppm. After completion of the reaction, 39.8 g of an aqueous solution of 30% PVP ("K-15" manufactured by Tokyo Kasei Kogyo Co., Ltd., molecular weight: 10,000) was added, followed by the addition of 24.0 g of a 5% sodium dodecylsulfate aqueous solution to obtain a concentrated vivid red-purple solution of gold colloid. The solution was then adjusted to pH4.7 to pH5.3 using hydrochloric acid or sodium hydroxide. The gold colloid solution was dried on a mesh with a collodion membrane attached thereto, followed by observing the dried gold colloid particles using a transmission electron microscope. Dispersion conditions of gold particles were excellent and the average particle diameter of the gold particles was about 18.5 nm. An absorption spectrum measured by a spectrophotometer confirmed the maximum absorption originating from gold plasmon absorption at 520-530 nm. The spectrum originating from the gold plasmon absorption is observed in nano-particles with a particle size in the range from several nm to several tens of nm. In addition, it is known that there is a very high correlation between the value of the maximum absorption wavelength and an average particle diameter. The change in the maximum absorption wavelength of this gold colloid solution was observed to confirm that the difference of the maximum absorption wavelength on the first day (day 0) and each day after day 0 was from −1.5 nm to +1.5 nm (mostly from −1.0 nm to +1.0 nm), and the gold colloid solution was stable for one year under the environment of 50° C.

Example 9

According to the method described in the WO 01/014047 pamphlet, a filter with a membrane area of 0.01 m$^2$ was prepared from a cuprammonium regenerated cellulose porous hollow fiber membrane with an average pore diameter of 18.5 nm.

The gold colloid solution of Example 8 was diluted to a gold colloid concentration of one-tenth using 0.27% sodium dodecylsulfate aqueous solutions with pH2.0, pH3.0, pH4.0, pH5.0, pH7.0, pH9.0, and pH11.0, followed by fine adjustment of pHs, and filtered using the constant-pressure dead-end method under a filtration pressure of 26.7 kPa The gold colloid concentration of 5 to 10 ml filtrate fraction was determined by absorbance measurement to calculate the LRV. The results are shown in Table 7.

The value of the LRV was about 2.3 in the range of pH4-11, indicating that the integrity test will result in a constant LRV value in this pH range.

Example 10

The solutions with pH4.0, pH5.0, pH7.0, pH9.0, and pH11.0 were prepared from the gold colloid solution obtained in Example 8 using hydrochloric acid or sodium hydroxide. Calcium chloride was added to the gold colloid solutions with different pHs. The resulting solutions were sufficiently stirred and allowed to stand overnight. The gold colloid solutions with pH4.0, pH5.0, pH7.0, pH9.0, and pH11.0 did not produce precipitates even when calcium chloride was added up to the concentration of 0.2 M.

Example 11

Figure 2:
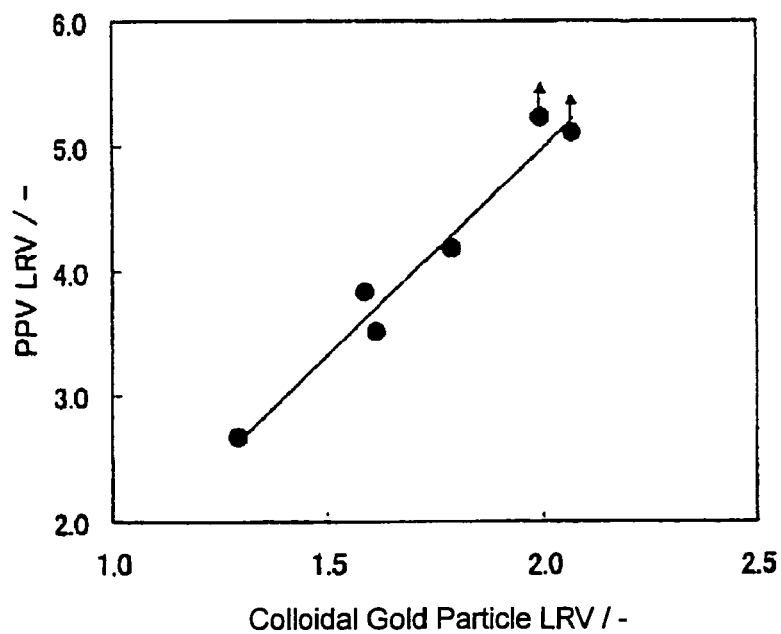
FIG. 2 is a diagram showing a correlation between removability of colloidal gold particles and removability of porcine parvoviruses. In this figure, the arrow indicates that the LRV is larger than the indicated value. The horizontal axis indicates "colloidal gold particle LRV", whereas the vertical axis indicates "porcine parvovirus (PPV) LRV".

According to the method described in the WO 01/014047 pamphlet, filters with a membrane area of 0.01 m$^2$ were prepared from cuprammonium regenerated cellulose porous hollow fiber membranes with different average pore diameter in the range from 18.0 nm to 21.0 nm. The diluted gold colloid solutions with pH4 to pH11 prepared in Example 9 were filtered using the above filters with different average pore diameter. As a filtration method, the constant-pressure dead-end method was conducted under a filtration pressure of 26.7 kPa The gold colloid concentration of 5 to 10 ml filtrate fraction was measured from the absorbance to calculate the LRV of the gold colloid. Porcine parvovirus (PPV) used as an indicator virus was added to D-MEM containing 5% fetal bovine serum so as to obtain a concentration of $10^{5.89}$ TCID$_{50}$/ml. The resulting solution was then filtered through the above filter with a membrane area of 0.01 m$^2$ made from the hollow fiber membranes with different pore diameters under a filtration pressure of 78.4 kPa. The virus concentration of 0 to 55 ml filtrate fraction was calculated as TCID$_{50}$/ml from the 50% cytopathic effect to ESK (porcine kidney) cells. The correlation between removability of gold colloid and removability of the virus is shown in FIG. 2. The results showed a good correlation, confirming that the metal colloid solution of the present invention can be applied to the integrity test of a virus removal membrane for removing small viruses.

Example 12

The gold colloid solution prepared in Example 1 was diluted to a gold colloid concentration of one-tenth using a 0.27% sodium dodecylsulfate (SDS) aqueous solution and filtered using the filter ("Planove 75N" manufactured by Asahi Kasei Pharma Corp.) with a membrane area of 0.01 m$^2$ made from a regenerated cellulose porous hollow fiber membrane with an average pore diameter of 75 nm. As a filtration method, the constant-pressure dead-end method was conducted under a filtration pressure of 26.7 kPa. The gold colloid concentration of 25 to 50 ml filtrate fraction (2.5 to 5.0 l/m$^2$) was measured from the absorbance to calculate the recovery rate of the metal colloid collection test. As a result, the recovery rate was 83.0%. The results are shown in Table 8.

Example 13

15 g of a 6.0 mM chloroauric acid aqueous solution and 385 g of distilled water were put into a reaction vessel (two batches). After heating to 100° C. while stirring, 8.5 to 9.0 g of a 3.0% sodium citrate aqueous solution was added into the vessel and the mixture was reacted for 60 minutes. The concentration of gold in the solution was about 90 ppm. After completion of the reaction, the reaction mixture was diluted with 350 ml of distilled water. 6.5 g of a 30% aqueous solution of PVP ("K-15" manufactured by Tokyo Kasei Kogyo Co., Ltd., molecular weight: 10,000) was added thereto, followed by the addition of 7.7 g of a 40 wt % sodium polyacrylate solution ("AC-103" manufactured by Nihonjunyaku Co., Ltd.) to prepare a gold colloid solution. An absorption spectrum measured by a spectrophotometer confirmed the maximum absorption at 529.4 nm. The aqueous solution was red. The gold colloid solution was dried on a mesh with a collodion membrane attached thereto, then the dried gold colloid particles were observed using a transmission electron microscope. The average particle diameter of the gold particles was about 16 nm to 17 nm.

Example 14

According to the method described in the WO 01/014047 pamphlet, a filter with a membrane area of 0.006 m$^2$ was prepared from a regenerated cellulose porous hollow fiber membrane with an average pore diameter of 29 nm. The gold colloid solution prepared by the method of Example 13 was filtered using the filter. As a filtration method, the dead-end method was conducted under a filtration pressure of 26.7 kPa.

The gold colloid concentration of 15 to 30 ml filtrate fractions (2.5 to 5.0 l/m$^2$) was determined by absorbance measurement to calculate the recovery rate of the metal colloid collection test. As a result, the recovery rate was 94.6%. The results are shown in Table 8.

Example 15

A composition containing 40 wt % of a polyvinylidene fluoride resin ("Sofef 1012" manufactured by Solvay, crystal melting point: 173° C.) and 60 wt % of dicyclohexyl phthalate (manufactured by Osaka Organic Chemical Industry Co., Ltd., industrial product) was stirred and mixed at 70° C. using a Henschel mixer, and was cooled to obtain a powdered product. The resulting product was charged in a twin-screw extruder ("Labo Plastomill Model 50C150" manufactured by Toyo Seiki Seisaku-Sho, Ltd.) via a hopper, and was uniformly dissolved by melting and mixing the product at 210° C. The dissolved product was extruded in the shape of a hollow fiber from a spinning nozzle formed of a circular orifice with an inner diameter of 0.8 mm and an outer diameter of 1.1 mm at a discharge rate of 17 m/min while causing dibutyl phthalate (manufactured by Sanken Kako Co., Ltd.) at 130° C. to flow at a rate of 8 ml/min inside the hollow. The extruded product was cooled and solidified in a water bath controlled the temperature at 40° C., and was wound at a rate of 60 l/min. After removing the dicyclohexyl phthalate and dibutyl phthalate by extraction with 99% methanol-modified ethanol (manufactured by Imazu Chemical Co., Ltd., industrial product), the adhering ethanol was replaced with water. The resulting product was subjected to a heat treatment at 125° C. for one hour using a high-pressure steam sterilizer ("HV85" manufactured by Hirayama Manufacturing Corporation) in a state in which the product was immersed in water. After replacing the adhering water with ethanol, the resulting product was dried at 60° C. in an oven to obtain a micro porous hollow fiber membrane. In the steps from extraction to drying, the membrane was treated while setting the membrane in a constant length state in order to prevent occurrence of shrinkage. The micro porous membrane was then subjected to a hydrophilic treatment using a grafting method. As the reaction liquid, a liquid obtained by dissolving hydroxypropyl acrylate (manufactured by Tokyo Kasei Kogyo Co., Ltd., reagent grade) in a 25 vol % aqueous solution of 3-butanol (reagent chemical manufactured by Junsei Kagaku Co., Ltd., guaranteed reagent), so that the hydroxypropyl acrylate content was 8 vol %, and bubbling nitrogen through the mixture at 40° C. for 20 min was used. The micro porous membrane was irradiated with γ-rays at 100 kGy from $^{60}$Co as the irradiation source in a nitrogen atmosphere while cooling the porous membrane to –60° C. with dry ice. The membrane after irradiation was allowed to stand under reduced pressure of 13.4 Pa or less for 15 minutes, caused to come in contact with the above reaction liquid at 40° C., and allowed to stand for one hour. After washing the membrane with ethanol, the membrane was dried at 60° C. for four hours under vacuum to obtain a hydrophilized PVDF porous hollow fiber membrane.

The average pore diameter of the resulting hydrophilized PVDF porous hollow fiber membrane was calculated using the following formula.

Average pore diameter of hydrophilized PVDF porous hollow fiber membrane=Average pore diameter of unhydrophilized PVDF porous hollow fiber membrane×((water permeation amount after hydrophilization)/(water permeation amount before hydrophilization))$^{1/4}$ The above unhydrophilized PVDF porous hollow fiber membrane is a membrane before hydrophilizing processing.

The water permeation amount of each membrane was calculated from the permeation amount of purified water at 25° C. measured by the constant-pressure dead-end method, membrane area, filtration pressure (0.1 MPa), and filtration time using the following formula.

[Water permeation amount (m$^3$/m$^2$/sec/Pa)=permeation amount÷(membrane area×differential pressure×filtration time)]

The resulting average pore diameter was 28.0 nm. The recovery rate of the metal colloid collection test was calculated according to the same method as in Example 14 (filtration pressure: 98 kPa) except for using the PVDF porous hollow fiber membrane. As a result, the recovery rate of gold colloid was 94.7%. The results are shown in Table 8.

Example 16

The recovery rate of the metal colloid collection test was calculated in the same manner as in Example 15 (filtration pressure: 98 kPa) except for using a solution of sodium acrylate-sodium methacrylate copolymer instead of the solution of sodium polyacrylate of Example 13. As a result, the recovery rate of gold colloid was 93.5%. The results are shown in Table 8.

Example 17

The recovery rate of the metal colloid collection test was calculated in the same manner as in Example 15 (filtration pressure: 98 kPa) except for using sodium tripolyphosphate (STPP) instead of the solution of sodium polyacrylate of Example 13. As a result, the recovery rate of gold colloid was 97.5%. The results are shown in Table 8.

Example 18

The recovery rate of the metal colloid collection test was calculated in the same manner as in Example 15 (filtration pressure: 98 kPa) except for using disodium ethylenediaminetetraacetate (EDTA-2Na) instead of the sodium polyacrylate of Example 13. As a result, the recovery rate of gold colloid was 87.4%. The results are shown in Table 8.

Example 19

The recovery rate of the metal colloid collection test was calculated in the same manner as in Example 15 (filtration pressure: 26.7 kPa), except for using filter MillexGV™ (membrane area: 0.00039 m$^2$, manufactured by Millipore) made from a flat hydrophlized PVDF porous membrane with an average pore diameter of 220 nm instead of the regenerated cellulose porous hollow fiber membrane. As a result, the recovery rate of gold colloid was 98.0%. The results are shown in Table 8.

Comparative Example 6

The recovery rate of the metal colloid collection test was calculated using the same method as in Example 15 (filtration pressure: 98 kPa) except for using sodium dodecylsulfate instead of the solution of sodium polyacrylate of Example 13. As a result, the gold colloid solution could not pass through and the recovery rate could not be measured.

Comparative Example 7

The recovery rate of the metal colloid collection test was calculated in the same manner as in Example 15 (filtration pressure: 98 kPa) except for using a gold colloid solution prepared without adding the solution of sodium polyacrylate of Example 13. As a result, the recovery rate of gold colloid was 55.4%. The results are shown in Table 8.

Comparative Example 8

The recovery rate of the metal colloid collection test was calculated in the same manner as in Example 15 (filtration pressure: 98 kPa) except for using a gold colloid solution prepared without adding the PVP (K-15) of Example 13. As a result, the gold colloid aggregated and the recovery rate could not be measured.

Example 20

80 g of a 6.0 mM chloroauric acid aqueous solution and 320 g of distilled water were put into a reaction vessel. After heating to 70° C. while stirring, 18.5 g of a 4.0% sodium citrate aqueous solution was added and the mixture was reacted for 60 minutes. The concentration of gold in the solution was about 500 ppm. After completion of the reaction, 37.5 g of a 30% aqueous solution of PVP ("K-15" manufactured by Tokyo Kasei Kogyo Co., Ltd., molecular weight: 10,000) was added, followed by the further addition of 9.0 g of a 40 wt % sodium polyacrylate solution ("AC-103" manufactured by Nihonjunyaku Co., Ltd.) to obtain a concentrated red gold colloid solution. 10 g of the concentrated gold colloid solution was diluted with an aqueous solution prepared by adding 1.8 g of a 40 wt % sodium polyacrylate solution ("AC-103" manufactured by Nihonjunyaku Co., Ltd.) to 88.2 g of distilled water to obtain a red gold colloid solution. An absorption spectrum measured by a spectrophotometer confirmed the maximum absorption originating from gold plasmon at 526 nm. The gold colloid solution was dried on a mesh with a collodion membrane attached thereto to observe the dried gold colloid particles using a transmission electron microscope. Dispersion conditions of gold particles were excellent and the average particle diameter of the gold particles was 19 nm.

Example 21

Figure 3:
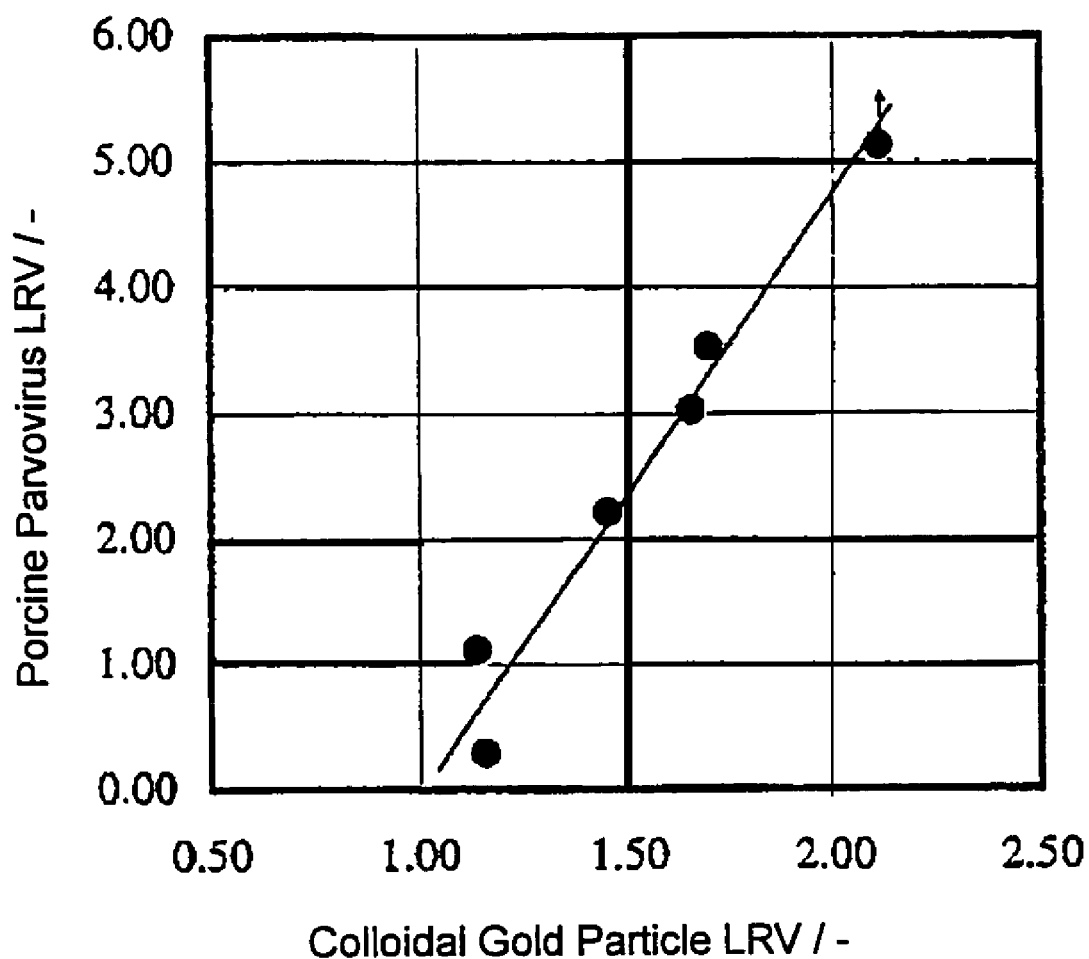
FIG. 3 is a diagram showing a correlation between removability of colloidal gold particles and removability of porcine parvoviruses using a PVDF porous hollow fiber membrane. In this figure, the arrow indicates that the LRV is larger than the indicated value. The horizontal axis indicates "colloidal gold particle LRV", whereas the vertical axis indicates "porcine parvovirus (PPV) LRV".

Hydrophilized PVDF porous hollow fiber membranes with different average pore diameters of 15.9 nm, 17.6 nm, 18.0 nm, 19.1 nm, 20.6 nm, and 21.2 nm were prepared by varying the concentration of the polyvinylidene fluoride of Example 15 to the range from 43 to 49%, and a filter with a membrane area of 0.01 m² was prepared. The gold colloid solution prepared by the method of Example 20 was filtered using the above filters with different average pore diameter. As a filtration method, the dead-end method was conducted under a filtration pressure of 98 kPa. The gold colloid concentration of 5 to 10 ml filtrate fractions was measured from the absorbance to calculate the LRV of the gold colloid. A parvovirus was used as an indicator virus, and added to D-MEM containing 5% fetal bovine serum at a concentration of $10^{6-7}$ $TCID_{50}$/ml. The gold colloid removability and virus removability showed a good correlation. The results are shown in FIG. 3. As a result, the gold colloid solution of the present invention can be applied to the integrity test of a virus removal membrane.

Example 22

80 g of a 6.0 mM chloroauric acid aqueous solution and 320 g of distilled water were put into a reaction vessel. After heating to 70° C. while stirring, 16.0 g of a 4.0% sodium citrate aqueous solution was added and the mixture was reacted for 60 minutes. The concentration of gold in the solution was 500 ppm. After completion of the reaction, 37.5 g of a 30% aqueous solution of PVP ("K-15" manufactured by Tokyo Kasei Kogyo Co., Ltd., molecular weight: 10,000) was added, followed by the addition of 9.0 g of a 40 wt % sodium polyacrylate solution ("AC-103" manufactured by Nihonjunyaku Co., Ltd.) to obtain a concentrated red gold colloid solution. 10 g of the concentrated gold colloid solution was diluted with an aqueous solution prepared by adding 1.8 g of a 40 wt % sodium polyacrylate solution ("AC-103" manufactured by Nihonjunyaku Co., Ltd.) to 88.2 g of distilled water to obtain a red gold colloid solution. An absorption spectrum measured by a spectrophotometer confirmed the maximum absorption originating from gold plasmon at 529 nm. The gold colloid solution was dried on a mesh with a collodion membrane attached thereto, then the dried gold colloid particles were observed using a transmission electron microscope. Dispersion conditions of gold particles were excellent and the average particle diameter of the gold particles was 21 nm.

Example 23

An distilled water (manufactured by Otsuka Pharmaceutical Co., Ltd.), 3 wt % cattle serum γ-globulin (manufactured by Invitrogen Corporation) (IgG), and a washing fluid to be used were maintained at 25° C. in advance. The 3wt % IgG solution was prefiltered using a filter ("Planove 35N" manufactured by Asahi Kasei Pharma Corp.) made from a regenerated cellulose porous hollow fiber membrane with an average pore diameter of 35 nm. All washing operations were carried out in a thermostat chamber at 25° C.

First, a hydrophilized PVDF porous hollow fiber membrane with an average pore diameter of 15.9 nm was prepared using polyvinylidene fluoride resin of Example 15 at a concentration of 49 wt %. Then, a filter with a membrane area of 0.01 m² was prepared. The 3wt % IgG was filtered using the filter under a filtration pressure of 294 kPa. The filtration was proceeded until the filtration speed reached ⅕ of the initial filtration speed, then the filter was reversely filtered with 0.1 M citric acid (manufactured by Wako Pure Chemical Industries, Ltd.) aqueous solution under a filtration pressure of 195 kPa for 5 minutes.

Then, the filter was reversely filtered with an injection solution under a filtration pressure of 195 kPa for 5 minutes to remove the washing fluid in the filter. The gold colloid solution prepared in Example 22 was filtered using the constant-pressure dead-end method under a pressure of 98 kPa. After 5 ml of gold colloid solution was caused to flow to replace the water in the filter, the subsequent 5 ml of filtrate was collected. The absorbance at 526 nm of the filtrate was measured using an absorbance meter (UV-1700 manufactured by Shimadzu Corp.) to calculate the logarithmic reduction value (LRV) of the gold colloid. The absorbance of a blank filter for which neither IgG filtration nor washing had been carried out was measured by the same method. As a result, the LRV of the filter was 2.03 and that of the blank filter was 2.01, confirming that an integrity test is possible.

Example 24

80 g of a 6.0 mM chloroauric acid aqueous solution and 320 g of distilled water were put into a reaction vessel. After heating to 70° C. while stirring, 16.0 g of a 4.0% sodium citrate aqueous solution was added and the mixture was reacted for 60 minutes. The concentration of gold in the solution was 500 ppm. After completion of the reaction, the reaction solution was cooled for 15 minutes in a water bath. 37.5 g of a 30% aqueous solution of PVP ("K-15" manufactured by Tokyo Kasei Kogyo Co., Ltd., molecular weight: 10,000) was added, followed by the addition of 9.0 g of a 40 wt % sodium polyacrylate solution ("AC-103" manufactured by Nihonjunyaku Co., Ltd.) to obtain a concentrated red gold colloid solution. 10 g of the concentrated gold colloid solution was diluted with an aqueous solution prepared by adding 1.8 g of a 40 wt % sodium polyacrylate solution ("AC-103" manufactured by Nihonjunyaku Co., Ltd.) to 80 g of the distilled water. The pH of the diluted solutions were adjusted to pH2.0, pH3.0, pH4.0, pH5.0, pH7.0, pH9.0, pH1.0, and pH12.0 using hydrochloric acid or sodium hydroxide. The distilled water was added to make 100 g of the total amount of each pH solution. The diluted gold colloid solutions were filtered using the constant-pressure dead-end method under a pressure of 98 kPa. 5 ml of the diluted gold colloid solution was caused to flow to replace the water in the filter. The subsequent 5 ml of filtrate was collected. The absorbance at 526 nm of the filtrate was measured using an absorbance meter ("UV-1700" manufactured by Shimadzu Corp.) to calculate the logarithmic reduction value (LRV) of the gold colloid. As a result, a value of the LRV of almost 2.0 was obtained in the range of pH4-11, indicating that the integrity test will result in a constant LRV value in this pH range.

Comparative Example 9

A gold colloid solution was prepared according the method described in JP-A-08-141388. 80 g of a 6.0 mM chloroauric acid aqueous solution was put into a reaction vessel. After the addition of 280 g of distilled water and 39.8 g of a 30% aqueous solution of PVP ("K-15", manufactured by Tokyo Kasei Kogyo Co., Ltd., molecular weight: 10,000), 14.9 g of a 4% sodium citrate aqueous solution was added and the mixture was reacted at 70° C. for 60 minutes. The concentration of gold in the solution was 500 ppm. After completion of the reaction, a concentrated purple red gold colloid was obtained. The resulting gold colloid was unhomogeneous with charcoal precipitate being observed in the bottom visually. This solution was divided into two solutions. A sodium dodecylsulfate solution was added to one solution so as to the final concentration of 0.27%. The both solutions, one containing sodium dodecylsulfate and the other not containing sodium dodecylsulfate, were adjusted to pH4.7 to pH5.3 using hydrochloric acid or sodium hydroxide. Portions of these gold colloid solutions were stored under an environment of 80° C. The difference in the maximum absorption wavelength after three days from that of day 0 was larger than 2.0 nm, indicating that the solution was unstable. After storing at room temperature for 180 days, the difference of the maximum absorption wavelength on the 180th day from that of day 0 was larger than 2.0 nm, also indicating that the solution was unstable. A homogeneous gold colloid solution could not be obtained by a production method in which the solution previously contains PVP when gold colloid particles are precipitated. In addition, such a solution was unstable during long term storage irrespective of the addition of sodium dodecyl sulfate.

Example 25

80 g of a 6.0 mM chloroauric acid aqueous solution and 320 g of distilled water were put into a reaction vessel. After heating to 70° C. while stirring, 16.0 g of a 4.0% sodium citrate aqueous solution was added and the mixture was reacted for 60 minutes. The concentration of gold in the solution was about 500 ppm. After completion of the reaction, 37.5 g of a 30% aqueous solution of PVP ("K-15" manufactured by Tokyo Kasei Kogyo Co., Ltd., molecular weight: 10,000) was added, followed by the addition of 9.0 g of a 40 wt % sodium polyacrylate solution ("AC-103" manufactured by Nihonjunyaku Co., Ltd.) to obtain a concentrated red gold colloid solution (pH7.5). The concentrated gold colloid solution was allowed to stand at 4° C., 25° C., or 50° C. to confirm the change of the gold colloid solution in the maximum absorption wavelength. As a result, the difference of the maximum absorption wavelength on the first day (day 0) and each elapsed day after day 0 was from −1.5 nm to +1.5 nm. The gold colloid solution was stable under the environment of 4° C., 25° C., and 50° C. for at least 90 days. In addition, stability for one year can be expected.

Example 26

Sodium dodecylsulfate was added to the concentrated gold colloid solutions to which PVP was added according to the method of Example 1 so as to exhibit the concentration of 0.14% or 1.0%, respectively. The solutions were adjusted to pH4.7 to pH5.3 using hydrochloric acid or sodium hydroxide. The concentrated gold colloid solutions containing sodium dodecylsulfate at a concentration of either 0.14% or 1.0% was diluted to one-tenth using aqueous solutions of sodium dodecylsulfate at a concentration of 0.14% or 1.0% to obtain diluted gold colloid solutions. The recovery rate of the metal colloid collection test was measured in the same manner as in Example 12 to confirm that the recovery rate using the gold solution containing 0.14% sodium dodecylsulfate was 75%. The recovery rate using the gold solution containing 1.0% sodium dodecylsulfate was 75% or more.

Example 27

Sodium polyacrylate was added to the gold colloid solutions to which PVP was added according to the method of Example 13 so as to exhibit a concentration of 0.08%, 2.0%, or 3.0%, respectively. Precipitate was observed in the gold colloid solution to which sodium polyacrylate was added at a concentration of 3.0%. The recovery rate of the metal colloid collection test was measured in the same manner as in Example 15 to confirm that the recovery rate using the gold colloid solution containing 0.08% sodium polyacrylate was 72%. The recovery rate using the gold colloid solution containing 2.0% sodium polyacrylate was 70% or more.

Example 28

According to the method of Example 1, PVP was added to the concentrated gold colloid solutions after completion of a reducing reaction so as to exhibit a concentration of 0.025% or 5.0%, respectively, followed by the addition of sodium dodecylsulfate to a concentration of 0.27%, thus obtaining concentration of 0.0025% or 5.0%. The solutions were adjusted to pH4.7 to pH5.3 using hydrochloric acid or sodium hydroxide. The gold colloid solutions were further diluted to one-tenth using a 0.27% sodium dodecylsulfate aqueous solution to obtain diluted gold colloid solutions containing PVP at a concentration of 0.025% or 0.5%.

TABLE 1

|  | Elapsed day (days) | | | |
| --- | --- | --- | --- | --- |
|  | 0 | 240 | 300 | 360 |
| Example 1 | 535.2 nm | 534.3 nm | 534.8 nm | 534.8 nm |
| Comparative Example 1 | 534.1 nm | 532.3 nm | 532.4 nm | 532.6 nm |

TABLE 2

|  | Elapsed day (days) | | |
| --- | --- | --- | --- |
|  | 0 | 4 | 6 |
| Example 2 | 533.6 nm | 533.5 nm | 533.6 nm |
| Comparative Example 2 | 534.3 nm | 527.6 nm | incapable measurement due to precipitation |

TABLE 3

|  | Example 3 | | | Comparative Example 3 | | |
| --- | --- | --- | --- | --- | --- | --- |
|  | Elapsed day (days) | | Difference of maximum absorption wavelength on day 180 from that on day 0 | Elapsed day (days) | | Difference of maximum absorption wavelength on day 180 from that on day 0 |
| pH | 0 | 180 |  | 0 | 180 |  |
| 2 | 530.2 nm | 530.8 nm | +0.6 nm | 524.9 nm | Could not be measured | Could not be measured |
| 3 | 530.2 nm | 530.8 nm | +0.6 nm | 524.6 nm | 524.5 nm | −0.1 nm |
| 4 | 529.8 nm | 530.2 nm | +0.4 nm | 523.8 nm | 523.8 nm | +0.0 nm |
| 5 | 529.8 nm | 529.9 nm | +0.1 nm | 523.6 nm | 524.1 nm | +0.5 nm |
| 7 | 529.7 nm | 529.2 nm | −0.5 nm | 523.4 nm | 525.7 nm | +2.3 nm |
| 9 | 529.4 nm | 529.0 nm | −0.4 nm | 523.3 nm | 525.4 nm | +2.1 nm |
| 11 | 528.9 nm | 528.8 nm | −0.1 nm | 522.9 nm | 525.5 nm | +2.6 nm |

TABLE 4

| pH | Example 4 | Comparative Example 4 |
| --- | --- | --- |
| 2 | Precipitated when adding calcium chloride up to 0.2 M | Precipitated when adding calcium chloride up to 0.04 M or less |
| 3 | | |
| 4 | Not precipitated when adding calcium chloride up to 0.2 M | |
| 5 | | |
| 9 | | |
| 11 | | |

TABLE 5

|  | Example 6 | | Comparative Example 5 | |
| --- | --- | --- | --- | --- |
| pH | LRV | pH | LRV | |
| 2 | 0.96 | 2 | 1.22 | |
| 3 | 1.45 | 3 | 1.34 | |
| 4 | 1.85 | 4 | 1.54 | |
| 5 | 2.13 | 5 | 1.76 | |
| 7 | 2.11 | 7 | 2.64 | |
| 9 | 2.06 | 9 | 2.92 | |
| 11 | 2.28 | 11 | 3.00 | |

TABLE 6

| Washing method | pH after last water washing | Water permeation recovery rate (%) | LRV of gold colloid |
| --- | --- | --- | --- |
| Wash with water, with NaOH + SDS, with HCl, and then with water | 5.3 | 97 | 2.1 |
| Wash with water, with NaOH + SDS, and then with water | 9.45 | 98 | 2.1 |
| Without protein filtration and washing | — | 100 | 2 |

TABLE 7

|  | Example 9 | |
| --- | --- | --- |
| pH | LRV | |
| 2 | 1.40 | |
| 3 | 1.86 | |
| 4 | 2.25 | |
| 5 | 2.34 | |
| 7 | 2.36 | |
| 9 | 2.36 | |
| 11 | 2.38 | |

TABLE 8

| | Surfactant or chelating agent | Water soluble high molecular weight dispersant containing a N group | Material of porous membrane | Recovery rate of gold colloid (%) |
|---|---|---|---|---|
| Example 12 | Sodium dodecylsulfate (SDS) | Poly(vinylpyrrolidone) ("K-15" manufactured by Tokyo Kasei Kogyo Co., Ltd.) | Regenerated cellulose hollow fiber | 83.0 |
| Example 14 | Sodium polyacrylate ("JURYMER AC103" manufactured by Nihonjunyaku Co., Ltd.) | Poly(vinylpyrrolidone) ("K-15" manufactured by Tokyo Kasei Kogyo Co., Ltd.) | Regenerated cellulose hollow fiber | 94.6 |
| Example 15 | Sodium polyacrylate ("JURYMER AC103" manufactured by Nihonjunyaku Co., Ltd.) | Poly(vinylpyrrolidone) ("K-15" manufactured by Tokyo Kasei Kogyo Co., Ltd.) | Hydrophilized PVDF hollow fiber | 94.7 |
| Example 16 | Sodium acrylate-sodium methacrylate copolymer ("JURYMER AC230" manufactured by Nihonjunyaku Co., Ltd.) | Poly(vinylpyrrolidone) ("K-15" manufactured by Tokyo Kasei Kogyo Co., Ltd.) | Hydrophilized PVDF hollow fiber | 93.5 |
| Example 17 | Sodium tripolyphosphate ("STPP" manufactured by Wako Pure Chemical Industries, Ltd.) | Poly(vinylpyrrolidone) ("K-15" manufactured by Tokyo Kasei Kogyo Co., Ltd.) | Hydrophilized PVDF hollow fiber | 97.5 |
| Example 18 | Disodium ethylenediaminetetraacetate ("EDTA-2Na" manufactured by Dojindo Laboratories Co., Ltd) | Poly(vinylpyrrolidone) ("K-15" manufactured by Tokyo Kasei Kogyo Co., Ltd.) | Hydrophilized PVDF hollow fiber | 87.4 |
| Example 19 | Sodium polyacrylate ("JURYMER AC103" manufactured by Nihonjunyaku Co., Ltd.) | Poly(vinylpyrrolidone) ("K-15" manufactured by Tokyo Kasei Kogyo Co., Ltd.) | Hydrophilized PVDF plane membrane | 99.7 |
| Comparative Example 6 | Sodium dodecylsulfate (SDS) | Poly(vinylpyrrolidone) ("K-15" manufactured by Tokyo Kasei Kogyo Co., Ltd.) | Hydrophilized PVDF hollow fiber | Could not be measured |
| Comparative Example 7 | None | Poly(vinylpyrrolidone) ("K-15" manufactured by Tokyo Kasei Kogyo Co., Ltd.) | Hydrophilized PVDF hollow fiber | 55.4 |
| Comparative Example 8 | Sodium polyacrylate ("JURYMER AC103" manufactured by Nihonjunyaku Co., Ltd.) | None | Hydrophilized PVDF hollow fiber | Could not be measured |

INDUSTRIAL APPLICABILITY

The colloid solution of the present invention exhibits excellent storage stability, pH stability, and the like, and useful as viral substitute particles for an integrity test for a virus removal membrane.

The invention claimed is:

1. A colloid solution of metal particles or metal compound particles being formed from one metal used in an integrity test for a virus removal membrane comprising:
(1) from 0.0001 to 0.1 wt % of metal particles or metal compound particles being formed from one metal having an average particle diameter of 15-40 nm,
(2) a water-soluble high molecular weight dispersant containing a pyrrolidone group,
(3) water, and
(4) an anionic surfactant and/or a chelating agent, wherein all of the metal particles or metal compound particles of the colloid solution are formed from said one metal have an average particle size diameter of 15-40 nm, and
the colloid solution has the following properties (a) and (b):
(a) a maximum absorption wavelength after 180 days storage at room temperature and at a constant pH in a range from pH4 to pH11 which differs from the maximum absorption wavelength prior to storage by −2.0 nm to +2.0 nm, and
(b) a maximum absorption wavelength after one year storage at 50° C. and at pH5 which differs from the maximum absorption wavelength prior to storage by −2.0 nm to +2.0 nm.

2. The colloid solution of metal particles or metal compound particles according to claim 1, wherein,
the metal particles or metal compound particles have a percent of variation in the particle diameter distribution of 30% or less, and
the colloid solution achieves a colloid recovery rate of 70% or more when the colloid solution is filtered through a collection test porous membrane and satisfies the following conditions:

(average pore diameter (nm) of the collection test porous membrane)−(average particle diameter (nm) of colloid)>10 nm.

3. A method for producing a colloid solution used in an integrity test according to claim 1, comprising: adding a water-soluble high molecular weight dispersant containing a pyrrolidone group to the colloid solution, and further adding an anionic surfactant and/or a chelating agent.

4. The method for producing a colloid solution according to claim 3, further comprising:
dissolving a metal compound in a solvent, causing the metal particles to form by reducing the metal compound,
then adding a water-soluble high molecular weight dispersant containing a pyrrolidone group, and
further adding an anionic surfactant and/or a chelating agent.

5. An integrity test method of a virus removal membrane for confirming the removability performance of the virus removal membrane comprising:
washing a virus removal membrane after use of the membrane for virus removal,
filtering the colloid solution according to claim 1 through the virus removal membrane which was used for virus removal, the colloid solution having a known absorbance at a maximum absorption wavelength,
measuring the absorbance of colloid solution at the maximum absorption wavelength after filtration, and
determining removability performance of the virus removal membrane based on the ratio of absorbance of the colloid solution measured before and after filtration.

6. The integrity test method according to claim 5, wherein the virus removal membrane is a porous cellulose membrane.

7. The integrity test method according to claim 5, wherein the virus removal membrane is a porous, thermoplastic synthetic polymer-membrane of which the surface is hydrophilized.

8. The integrity test method according to claim 7, wherein the thermoplastic polymer is polyvinylidene fluoride or polyether sulfone.

9. The integrity test method according to claim 5, achieving a colloid recovery rate of 70% or more when the colloid solution is filtered through a collection test porous membrane made of the same material as the virus removal membrane and satisfying the following conditions:

(average pore diameter (nm) of the collection test porous membrane)−(average particle diameter (nm) of colloid)>10 nm.

10. The integrity test method according to claim 5, wherein the one metal is selected from the group consisting of gold, silver, platinum, rhodium, palladium, ruthenium, iridium, osmium, iron, and copper.

11. The integrity test method according to claim 5, wherein the average particle diameter of metal particles or metal compound particles is 15 to 40 nm and the percent of variation in the particle diameter distribution is 30% or less.

12. The integrity test method according to claim 5, wherein the water-soluble high molecular weight dispersant containing the pyrrolidone group is poly(vinylpyrrolidone) or a poly(vinylpyrrolidone)copolymer.

13. The integrity test method according to claim 6, wherein the surfactant is dodecylsulfuric acid or its salt.

14. The integrity test method according to claim 6, wherein the chelating agent comprises at least one of tripolyphosphoric acid, polyacrylic acid, polyacrylic acid copolymer, ethylenediaminetetraacetic acid, and salts thereof.

15. The integrity test method according to claim 5, wherein the colloid solution is filtered after the membrane is washed using an alkali solution, but is not neutralized with an acid.

* * * * *